(12) United States Patent
Grant et al.

(10) Patent No.: US 9,091,695 B2
(45) Date of Patent: Jul. 28, 2015

(54) METHODS AND SYSTEMS FOR QUANTIFICATION OF PEPTIDES AND OTHER ANALYTES

(75) Inventors: Russell Philip Grant, Chapel Hill, NC (US); Andrew Dennis Wagner, Newington, CT (US)

(73) Assignee: Laboratory Corporation of America Holdings, Burlington, NC (US)

( * ) Notice: Subject to any disclaimer, the term of this patent is extended or adjusted under 35 U.S.C. 154(b) by 345 days.

(21) Appl. No.: 12/156,391

(22) Filed: May 30, 2008

(65) Prior Publication Data

US 2009/0090856 A1 Apr. 9, 2009

Related U.S. Application Data

(60) Provisional application No. 60/932,770, filed on Jun. 1, 2007.

(51) Int. Cl.
| | | |
|---|---|---|
| *G01N 24/00* | (2006.01) | |
| *G01N 33/68* | (2006.01) | |
| *G01N 33/76* | (2006.01) | |

(52) U.S. Cl.
CPC ............ *G01N 33/6848* (2013.01); *G01N 33/76* (2013.01)

(58) Field of Classification Search
None
See application file for complete search history.

(56) References Cited

U.S. PATENT DOCUMENTS

| | | | |
|---|---|---|---|
| 5,447,553 A | 9/1995 | Apffel, Jr. et al. | |
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,339,218 B1 | 1/2002 | Kato et al. | |
| 6,410,913 B1 | 6/2002 | Brekenfeld et al. | |
| 6,437,327 B2 | 8/2002 | Takada et al. | |
| 6,541,263 B2 | 4/2003 | Gao | |
| 6,635,173 B2 | 10/2003 | Brann | |
| 6,802,967 B2 * | 10/2004 | Masuda et al. | 210/198.2 |
| 6,808,635 B2 | 10/2004 | Brann | |
| 7,439,074 B2 * | 10/2008 | Nguyen et al. | 436/173 |
| 8,642,351 B2 * | 2/2014 | Liu et al. | 436/161 |
| 2002/0076739 A1 * | 6/2002 | Aebersold et al. | 435/7.92 |
| 2002/0084222 A1 | 7/2002 | Brann | |
| 2002/0155614 A1 * | 10/2002 | Tomlinson et al. | 436/86 |
| 2003/0015019 A1 | 1/2003 | O'Brien | |
| 2004/0235188 A1 | 11/2004 | Soldin | |
| 2004/0235193 A1 | 11/2004 | Soldin | |
| 2005/0161399 A1 | 7/2005 | Dillon et al. | |
| 2008/0070832 A1 * | 3/2008 | Valax et al. | 514/8 |

FOREIGN PATENT DOCUMENTS

| | | |
|---|---|---|
| WO | WO 03/089921 A1 | 10/2003 |
| WO | WO 2004/090525 A1 | 10/2004 |
| WO | WO 2004/090553 A1 | 10/2004 |

OTHER PUBLICATIONS

Myers, Tanya R., New Techniques for the Qualitative and Quantitaive Measurement of Naturally-Occurring Gonadotropin-Releasing Hormone Analogues by Mass Spectrometry, May 2007, Chemistry Dissertations. Paper 12.*

Myers et al., A new strategy utilizing electrospray ionization-quadrupole ion trap mass spectrometry for the qualitative determination of GnRH peptides, Journal of Mass Spectrometery, Jul. 2006; 41, pp. 950-959.*

Reichmuth et al., Microchip HPLC of Peptides and Proteins, Anal. Chem. 2005, 77, pp. 2997-3000.*

Lindner et al., Application of hydrophilic-interaction liquid chromatography to the separation of phosphorylated H1 histones, Journal of chromatography a, 782, 1997, pp. 55-62.*

Opiteck et al., Comprehensive On-Line LC/LC/MS of Proteins, Anal. Chem. 1997, 69, pp. 1518-1524.*

Anari, M. et al., Derivation of ethinylestradiol with dansyl chloride to enhance electrospray ionization: application in trace analysis of ethinylestradiol in rhesus monkey plasma, Anal. Chem., vol. 74, No. 16, pp. 4136-4144, 2002.

Budzinski, H. et al., Analysis of hormonal steroids in fish plasma and bile by coupling solid-phase extraction to gc/ms, Anal. Bioanal. Chem., vol. 386, pp. 1429-1439, 2006.

Draisci, R. et al., Quantification of 17 β-estradiol residues n bovine serum by liquid chromatography-tandem mass spectrometry with atmospheric pressure chemical ionization, vol. 123, 1998 pp. 2605-2609.

Dugo, P. et al., Comprehensive Tow Dimensional Normal Phase (Adsorption)-Reversed-Phase Liquid Chromatography, Anal. Chem., vol. 76, No. 9, pp. 2525-2530, 2004.

Fedeniuk, R. et al., Validaiotn of a gas chromatography mass spectrometry method for the determination of pg/ml levels of 17 β-estradiol and 17 β-trenbolone in bovine serum, J. Chromatogr B. Analyt Technol Biomed Life Sci., vol. 802, No. 2, pp. 307-315, 2004.

Ferretti, G. et al., Simultaneous analysis of 17 α-estradiol and 17β-estradiol in bovine serum by liquid chromatography-tandem mass spectrometry, Journal of Chormatography B, vol. 871, pp. 135-140, 2008.

Guo, T. et al., Steroid profiles using liquid chromatography-tandem mass spectrometry with atmospheric pressure photoionization source, Arch. Pathol. Lab. Med., vol. 128, No. 4, pp. 469-475, 2004.

Higashi, T. et al., Procedure for increasing the detection responses of estrogens in lc-ms based on introduction of a nitrobenzene moiety followed by electron capture atmospheric pressure chemical ionization, Anal. Bioanal. Chem., vol. 386, pp. 658-665, 2006.

(Continued)

*Primary Examiner* — Gary W Counts
(74) *Attorney, Agent, or Firm* — Kilpatrick Townsend & Stockton, LLP

(57) ABSTRACT

Disclosed are LC-LC-MS/MS techniques for the analysis of endogenous peptides and other highly polar small molecules. The methods and systems of the present invention can be applied in all industries that utilize LC-MS/MS for the evaluation and quantification of biological analytes in complex matrixes.

28 Claims, 29 Drawing Sheets
(11 of 29 Drawing Sheet(s) Filed in Color)

(56) References Cited

OTHER PUBLICATIONS

Jandera, P. et al., Two-dimensional liquid chromatography normal-phase and reversed-phase separation of (co)oligomers, Journal of Chromatography A, vol. 1119, pp. 3-10, 2006.
Kawaguchi, M. et al., Dual derivatization-stir bar sorptive extraction-thermal desorption-gas chromatography-mass spectrometry for determination of 17β-estradiol in water sample, Journal of Chromatography A, vol. 1105, pp. 140-147, 2006.
Nelson, R. et al., Liquid chromatography-tandem mass spectrometry assay for simultaneous measurements of estradiol and estrone in human plasma, Clinical Chemistry, vol. 50, No. 2, pp. 373-384, 2004.
Tai, S. et al., Development and evaluation of a reference measurement procedure for the determination of estradiol-17β in human serum using isotope-dilution liquid chromatography-tandem mass spectrometry, Anal. Chem., vol. 77, No. 19, pp. 6359-6363, 2005.
Wu, H. et al., Serum estradiol quantification by isotope dilution-gas chromatography/mass spectrometry, Technical Briefs, Abbott Laboratories, Abbott Park, IL. Clin. Chem 48, No. 2 2002, pp. 364-366.
Xu, X. et al., Measuring fifteen endogenous estrogens simultaneously in human urine by high-performance liquid chromatography-mass spectrometry, Anal. Chem., vol. 77, No. 20, pp. 6646-6654, 2005.
Zacharia, L. et al., A gas chromatography/mass spectrometry assay to measure estradiol, catecholestradiols, and methoxyestradiols in plasma, Steroids, vol. 69, pp. 255-261, 2004.
Zhang, H. et al., Quantitative and qualitative determination of estrogen sulfates in human urine by liquid chromatography/tandem mass spectrometry using 96-well technology, Anal. Chem., vol. 71, No. 18, pp. 3955-3964, 1999.
de Alda, M. et al., Liquid chromatography-(tandem) mass spectrometry of selected emerging pollutants (steroid sex hormones, drugs and alkylphenolic surfactants) in the aquatic environment, Journal of Chromatography A, vol. 1000, pp. 503-526, 2003.
de Alda, M. et al., Chapter 11: Analysis of selected emerging pollutants (steroid sex hormones, drugs and alkylphenolic surfactants) in the aquatic environment by lc-ms and lc-ms-ms, Department of Environmental Chemistry, Barcelona Spain.
Antignac, J. et al., Collision-induced dissociation of corticosteroids in electrospray tandem mass spectometry and development of a screening method by high performance liquid chromatography/tandem mass spectrometry, Rapid communications in Mass Spectrometry, vol. 14, pp. 33-39, 2000.
Asperger, A. et al., Trace determination of priority pesticides in water by means of high-speed on-line solid-phase extraction-liquid chromatography-tandem mass spectrometry using turbulent-flow chromatography colums for enrichment and a short monolithic column for fast liquid chromatographic separation, Journal of Chromatography A, vol. 960, pp. 109-119, 2002.
Ayrton, J. et al., Ultra-high flow rate capillary liquid chromatography with Mass Spectrometric detection for the direct analysis of pharmaceuticals in plasma at sub-nanogram per millilitre concentrations, Rapid Communications in Mass Spectrometry, vol. 13, pp. 1657-1662, 1999.
Carignan, G. et al., High-performance liquid chromatographic analysis of estradiol valerate-testosterone enanthate in oily formulations, Journal of Chromatography, vol. 301, pp. 292-296, 1984.
Chang, Y. et al., Quantitative measurement of male steroid hormones using automated on-line solid phase extraction-liquid chromatography-tandem mass spectrometry and comparison with radioimmunoassay, Analyst, vol. 128, pp. 363-368, 2003.
Choi, M. et al., Rapid HPLC-electrospray tadem mass spectrometric assay for urinary testosterone and dihydrotestosterone glucuronides from patients with benign prostate hyperplasia, Clinical Chemistry, vol. 49, No. 2, pp. 322-325, 2003.
Choi, M. et al., Determination of four anabolic steroid metabolites by gas chromatography/mass spectrometry with negative ion chemical ionization and tandem mass spectrometry, Rapid Communications in Mass Spectrometry, vol. 12, pp. 1949-1755, 1998.

Dorgan, J. et al., Measurement of steroid sex hormones in serum, a comparison of radioimmunoassay and mass spectrometry, Steroids, vol. 67, pp. 151-158, 2002.
Draisci, R. et al., Quantitation of anabolic hormones and their metabolites in bovine serum and urine by liquid chromatography-tandem mass spectrometry, Journal of Chromatography A, Vo.. 870, pp. 511-522, 2000.
Friedrich, G. et al., Determination of testosterone metabolites in human hepatocytes I. development of an in-line sample preparation liquid chromatography technique and mass spectroscopic detection of 6β-hydroxytestosterone, Journal of Chromatography A, vol. 784, pp. 49-61, 2003.
Furuta, T. et al., Simultaneous measurements of endogenous and deuterium-labelled tracer variants of androstenedione and teststerone by capillary gas chromatography-mass spectrometry, Journal of Chromatography, vol. 525, pp. 15-23, 1990.
Giraudi, G. et al., Effect of tracer binding to serum proteins in the reliability of a direct free testosterone assay, Steroids, vol. 52, No. 4, pp. 423-424, 1988.
Grant, R. et al., Generic serial and parallel on-line direct-injection using turbulent flow liquid chromatography/tandem mass spectrometry, Rapid Communications in Mass Spectrometry, vol. 1, pp. 1785-1792, 2003.
Griffiths, W. et al., Derivatisation for the characterisation of neutral oxosteroids by electrospray and matrix-assisted laser desorption/ionisation tandem mass spectrometry: the Girard P derivative, Rapid Communications in Mass Spectrometry, vol. 17, pp. 924-935, 2003.
Jemal, M. et al., Comparison of plasma sample purification by manual liquid-liquid extraction and automated 96-well solid-phase extraction for analysis by high-performance liquid chromatography with tandem mass spectrometry, Journal of Chromatography B, vol. 732, pp. 501-508, 1999.
Kim, J. et al., Measurement of 19-nortestosterone and its esters in equine plasma by high-performance liquid chromatography with tandem mass spectrometry, Rapid Communications in Mass Spectrometry, vol. 14, pp. 1835-1840, 2000.
Lagana, A. et al., Liquid chromatography tandem mass spectrometry applied to the analysis of natural and synthetic steroids in environmental waters, Analytical Letters, vol. 34, No. 6, pp. 913-926, 2001.
Lewis, R. et al., A novel method for the determination of sildenafil (viagra) and its metabolite (uk-103,320) in postmortem specimens using lc/ms/ms and lc/ms/ms/ms, Office of Aviation Medicine, Washington, D.C., May 2000.
Li, H. et al., A high-performance-liquid-chromatography-based method for the determination of hydroxylated testosterone metabolites formed in vitro liver microsomes from gray seal (*Halichoerus grypus*), Journal of Chromatographic Science, vol. 40, pp. 397-402, 2002.
Merchant, M. et al., Recent advancements in surface-enhanced laser desorption/ionization-time of flight-mass spectrometry, Electrophoresis, vol. 21, pp. 1164-1167, 2000.
ropero-Miller, J. et al., Simultaneous quantitation of opioids in blood by gc-ei-ms analysis following deproteination, detautomerization of keto analytes, solid-phase extraction, and trimethylsilyl derivatization, Journal of Analytical Toxicology, vol. 26, pp. 524-528, 2002.
Monnoyer, S. et al., Development of a high-performance liquid chromatography-tandem mass spectrometry method for the determination of flurogestone acetate in ovine plasma, Journal of Chromatography B, vol. 819, pp. 245-251, 2005.
Navajas, R. et al., Determination of epitestosterone and testosterone in urine by high performance liquid chromatography, Journal of Chromatography B, vol. 673, pp. 159-164, 1995.
Ng, B. et al, Determination of plasma testosterone using a simple liquid chromatographic method, Journal of Chromatography B, vol. 793, pp. 421-426, 2003.
Oka, K. et al., Combined use of rapid flow fractionation and high-performance liquid chromatography for the determination of serum testosterone and application to study of stress response to physical exercise, Journal of Chromatography, vol. 423, pp. 285-291, 1987.
Robb, D. et al., Atmospheric pressure photoionization: an ionization method for liquid chromatography-mass spectrometry, Anal. Chem, vol. 72, pp. 3653-3659, 2000.

(56) References Cited

OTHER PUBLICATIONS

Starcevic, B. et al., Liquid chromatography-tandem mass spectrometry assay for human serum testosterone and trideuterated testosterone, Journal of Chromatography B, vol. 792, pp. 197-204, 2003.

Tachibana, S. et al., Simultaneous determination of testosterone metabolites in liver microsomes using column-switching semi-microcolumn high performance liquid chromatography, Analytical Biochemistry, vol. 295, pp. 248-256, 2001.

Tiller, P. et al., Drug quantitation on a benchtop liquid chromatography-tandem mass spectrometry system, Journal of Chromatography A, vol. 771, pp. 119-125, 1997.

Wang, D. et al., Rapid quantitation of testosterone hydroxyl metabolites by ultra-performance liquid chromatography and mass spectrometry, Journal of Chromatography B, vol. 855, pp. 290-294, 2007.

Wright, G. et al., Proteinchip surface enhanced laser desorption/ionization (seldi) mass spectrometry: a novel protein biochip technology for detection of prostate cancer biomarkers in complex protein mixtures, Prostate Cancer and Prostate Disease, vol. 2, pp. 264-276, 1999.

Williams, T. et al., Electrospray collision-induced dissociation of testosterone and testosterone hydroxy analogs, Journal of Mass Spectrometry, vol. 34, pp. 206-216, 1999.

Yost, Tandem Mass Spectrometry, Chapter 8, Ed. McLafferty, John Wiley and Sons: 1983.

Xia, Y. et al., Ternary-column system for high-throughput direct-injection bioanalysis by liquid chromatography/tandem mass spectrometry, Rapid Communications in Mass Spectrometry, vol. 14, pp. 105-111, 2000.

Zimmer, D. et al., Comparison of turbulent-flow chromatography with automated solid-phase extraction in 96-well plates and liquid-liquid extraction used as plasma sample preparation techniques for liquid chromatography-tandem mass spectrometry, Journal of Chromatography A, vol. 854, pp. 23-35, 1999.

Patent Cooperation Treaty, International Search Report and Written Opinion, International Application No. PCT/US2008/006908, mailed Sep. 12, 2008.

Patent Cooperation Treaty, International Search Report and Written Opinion, International Application No. PCT/US07/012525 mailed Jul. 2, 2008.

Alpert AJ, "Hydrophilic-interaction chromatography for the separation of peptides, nucleic acids and other polar compounds," Journal of Chromatography, 499: 177-96 (1990).

* cited by examiner

Molecular Structure

SPE Elution Profile

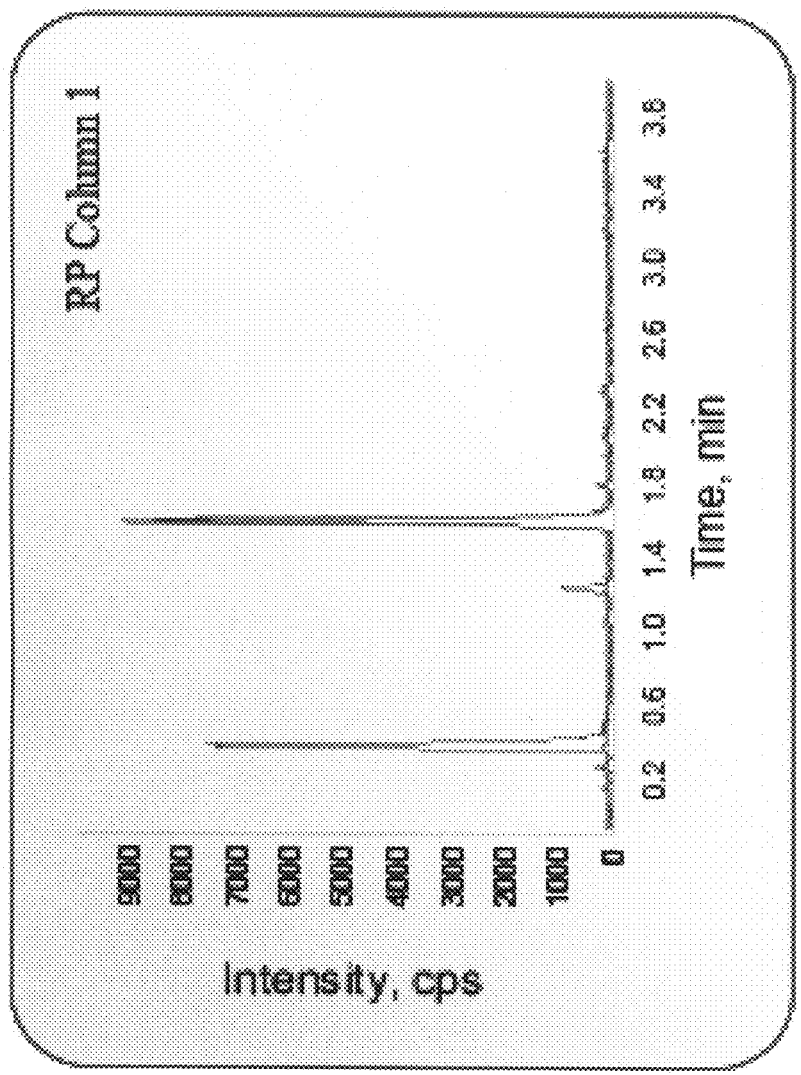

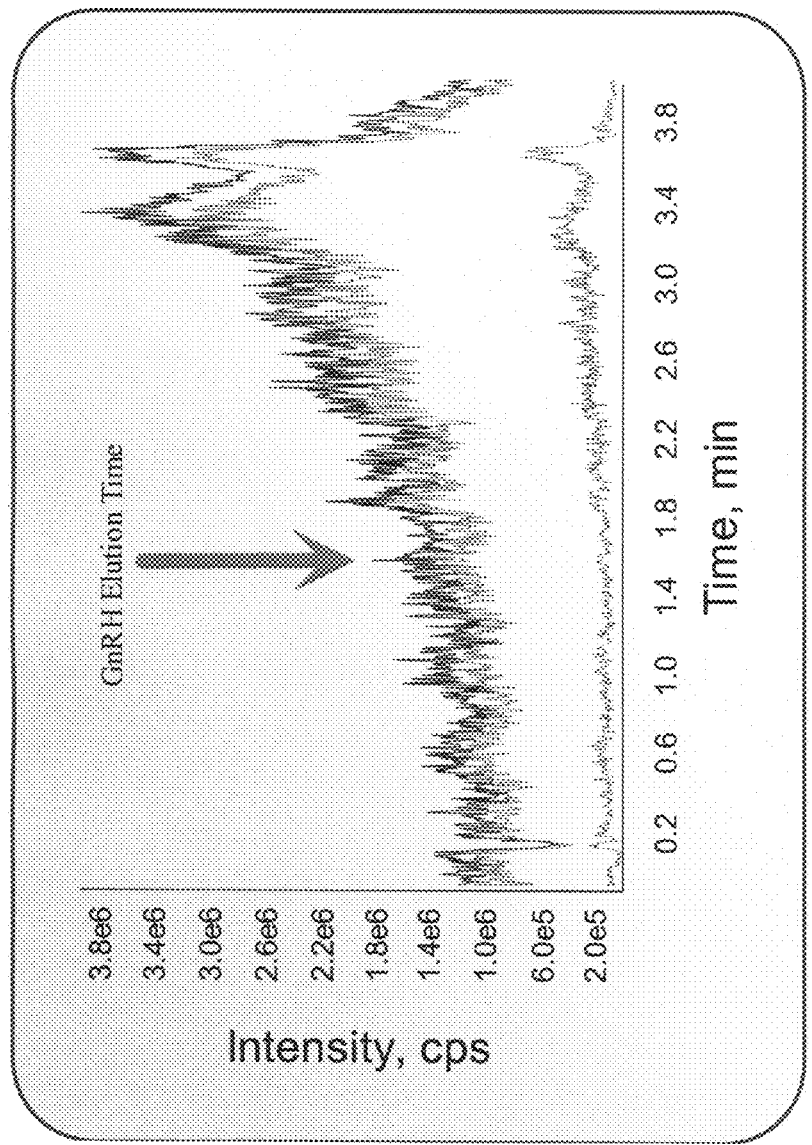
FIG. 5B Water Injection

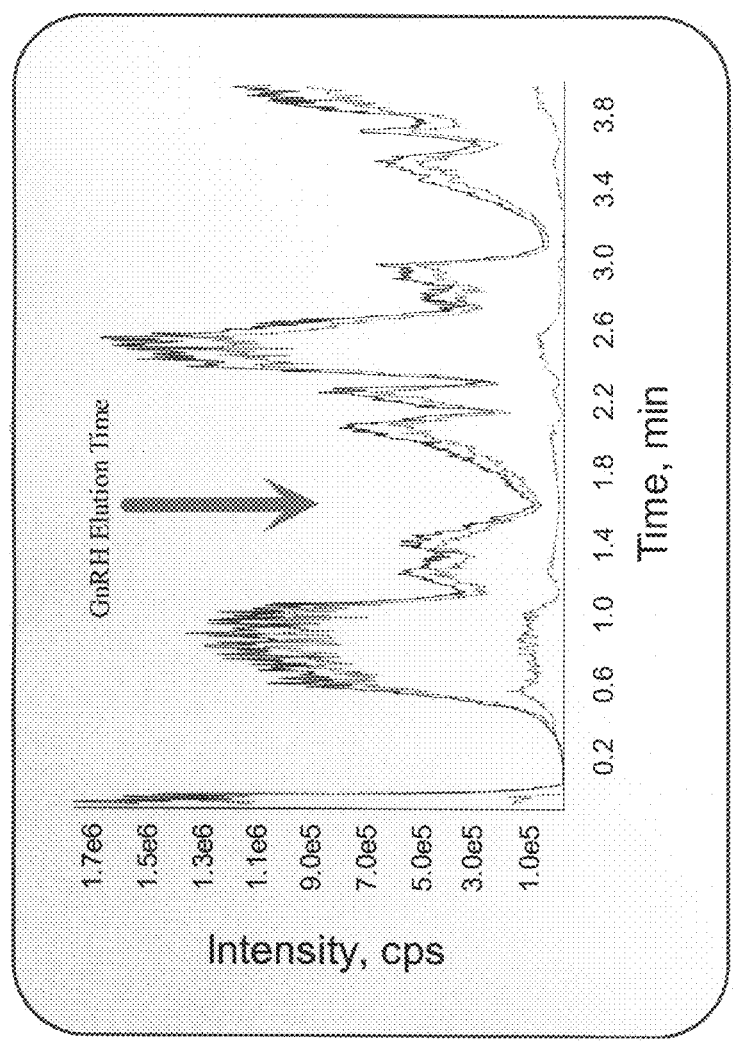

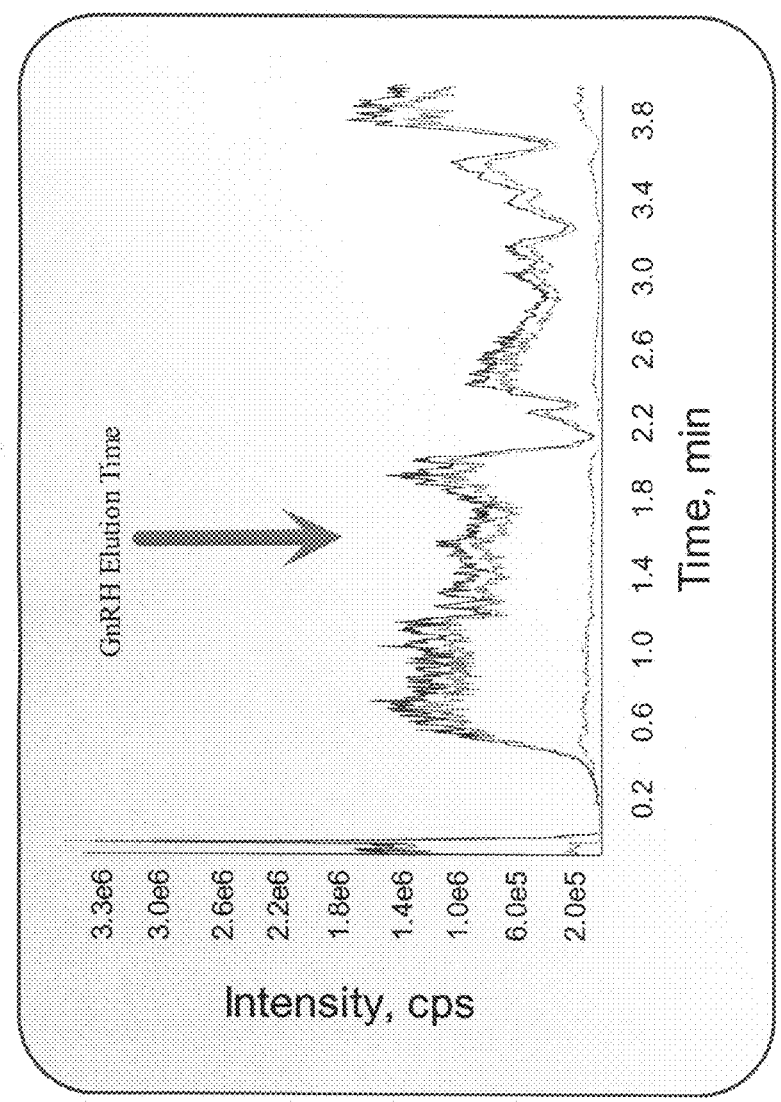
FIG. 5D Plasma (Acetonitrile Ppt)

GnRH (5ng/mL)

Water Injection

Plasma (Methanol Ppt)

Calibration Curve

Cross-Validation

| Conc. (pg/mL) | Accuracy (%) | | | Precision (%) | | | |
|---|---|---|---|---|---|---|---|
| | 10 | 500 | 1000 | 30 | 100 | 400 | 800 |
| Intra - 1 | -4.9 | 0.7 | -1.4 | 3.5 | 1.7 | 1.5 | 1.9 |
| Intra - 2 | 0.5 | -1.1 | -1.1 | 3.5 | 3.3 | 2.8 | 2.9 |
| Intra - 3 | -8.3 | -1.0 | -1.7 | 6.4 | 3.1 | 3.2 | 1.8 |
| Inter | -4.2 | -0.5 | -1.4 | 4.6 | 2.8 | 2.6 | 2.2 |

Accuracy and Precision

FIG. 9A

| Validation | Bias (%) |
|---|---|
| Plasma | 2.5 – 3.7 |
| Lipemia | 6.6 |
| Whole Blood | 16.2 |
| Recovery | 97.9 – 106.8 |

Matrix Effect/Recovery

FIG. 9B

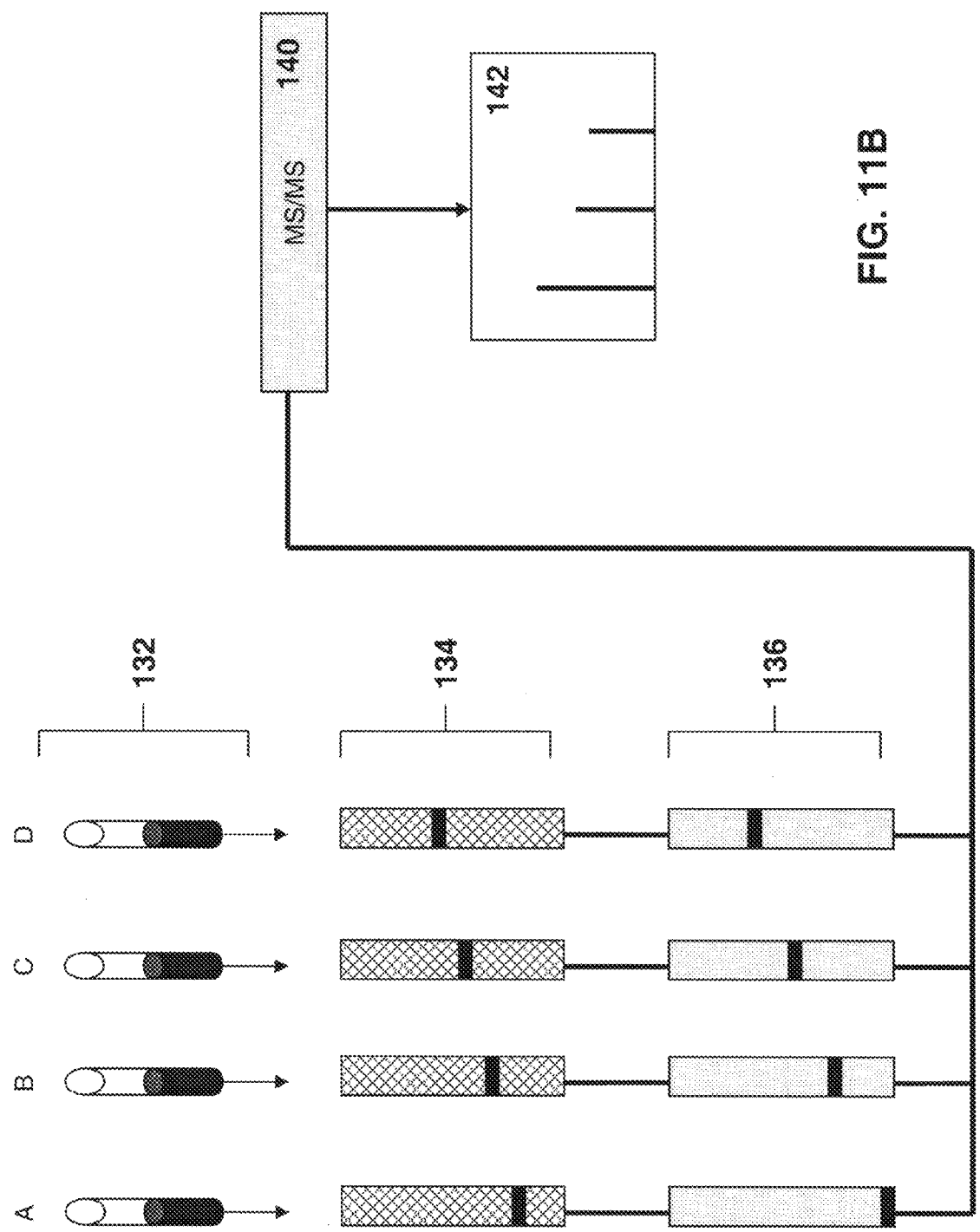

METHODS AND SYSTEMS FOR QUANTIFICATION OF PEPTIDES AND OTHER ANALYTES

CROSS REFERENCE TO RELATED APPLICATIONS

The present application claims priority under 35 USC 119 (e) from U.S. Provisional Patent Application Ser. No. 60/932,770, filed Jun. 1, 2007. The disclosure of U.S. Provisional Patent Application Ser. No. 60/932,770 is hereby incorporated by reference in its entirety herein.

FIELD OF INVENTION

The present invention relates to methods and systems for quantification of peptides and other analytes.

BACKGROUND

Imbalances in polypeptide hormones can be important in a variety of health disorders. For example, GnRH (or LHRH) is a hormone normally found in the portal circulation between the hypothalamus and the pituitary. This 10 amino acid (AA) neuropeptide is made in the hypothalamus from a large precursor protein. Gonadotropin Releasing Hormone (GnRH) is a hormone normally found in the portal circulation between the hypothalamus and the pituitary. Pulsatile release of the decapeptide up-regulates and stimulates receptors, conversely continuous exposure down-regulates receptors. Receptors for GnRH are found on pituitary gonadotrophs where GnRH stimulates the release of luteinizing hormone (LH) and follicle stimulating hormone (FSH), hormones that are important in maintaining the reproductive function. GnRH secretion at the onset of puberty triggers sexual development, and is essential for normal sexual physiology of both males and females. In both sexes, its secretion occurs in periodic pulses usually occurring every 1-2 hours.

Circulating levels of GnRH are typically too low to measure accurately via radioimmunoassay, and quantification of peptides via traditional LC-MS/MS can be challenging. Traditionally, three methods have been used to measure peptides such as GnRH: (1) ion exchange chromatography followed by reverse phase liquid chromatography; (2) two-dimensional gel electrophoresis with excision of the peptide and further purification (e.g., liquid chromatography); and (3) antibody capture, which requires antibodies to the peptide, and subsequent purification of the peptide from the antibody. Generally, these methods are lacking in sensitivity and are too time-consuming for a high-throughput clinical assay. Thus, there is a need to develop methods to measure such peptide hormones.

SUMMARY

Embodiments of the present invention comprise methods and systems to measure peptides and other analytes. The present invention may be embodied in a variety of ways.

In certain embodiments, the methods and systems of the present invention comprise liquid chromatography in combination with mass spectrometry. For example, in one embodiment, the present invention comprises a method for determining the presence or amount of an analyte in a sample comprising chromatographically separating the analyte from other components in the sample using at least one of reverse phase liquid chromatography or hydrophilic interaction liquid chromatography. The method may also comprise analyzing the chromatographically separated analyte by mass spectrometry to determine the presence or amount of the analyte in the sample. Also, the method may comprise the step of providing a sample believed to contain the analyte.

The liquid chromatography may, in certain embodiments, of both the methods and systems of the present invention, comprise extraction liquid chromatography (LC) and/or analytical LC. In an embodiment, the extraction LC is reverse phase liquid chromatography (RPLC). Also in an embodiment, the analytical LC is hydrophilic interaction liquid chromatography (HILIC). For example, in one embodiment, the liquid chromatography may comprise reverse phase extraction LC followed by HILIC. The mass spectrometry may comprise tandem mass spectrometry (MS/MS). The method may further comprise a partial purification of the analyte of interest. For example, where the analyte is the peptide GnRH, liquid-liquid extraction (LLE) may be used prior to chromatography. The LLE may, in certain embodiments, comprise extraction of GnRH with acetonitrile. Also, embodiments of the present invention comprises systems for performing the methods of the invention. The methods and systems may be computer controlled for automation and high throughput.

Certain objects of the present invention, having been stated hereinabove, will become further evident as the description proceeds when taken in connection with the accompanying figures and examples as described herein below.

BRIEF DESCRIPTION OF THE DRAWINGS

The file of the is patent contains at least one drawing executed in color. Copies of this patent or patent application publication with color drawing(s) will be provided by the Office upon request and payment of the necessary fee.

Having thus described the invention in general terms, reference will now be made to the accompanying drawings, which are not necessarily drawn to scale.

Figure 1:
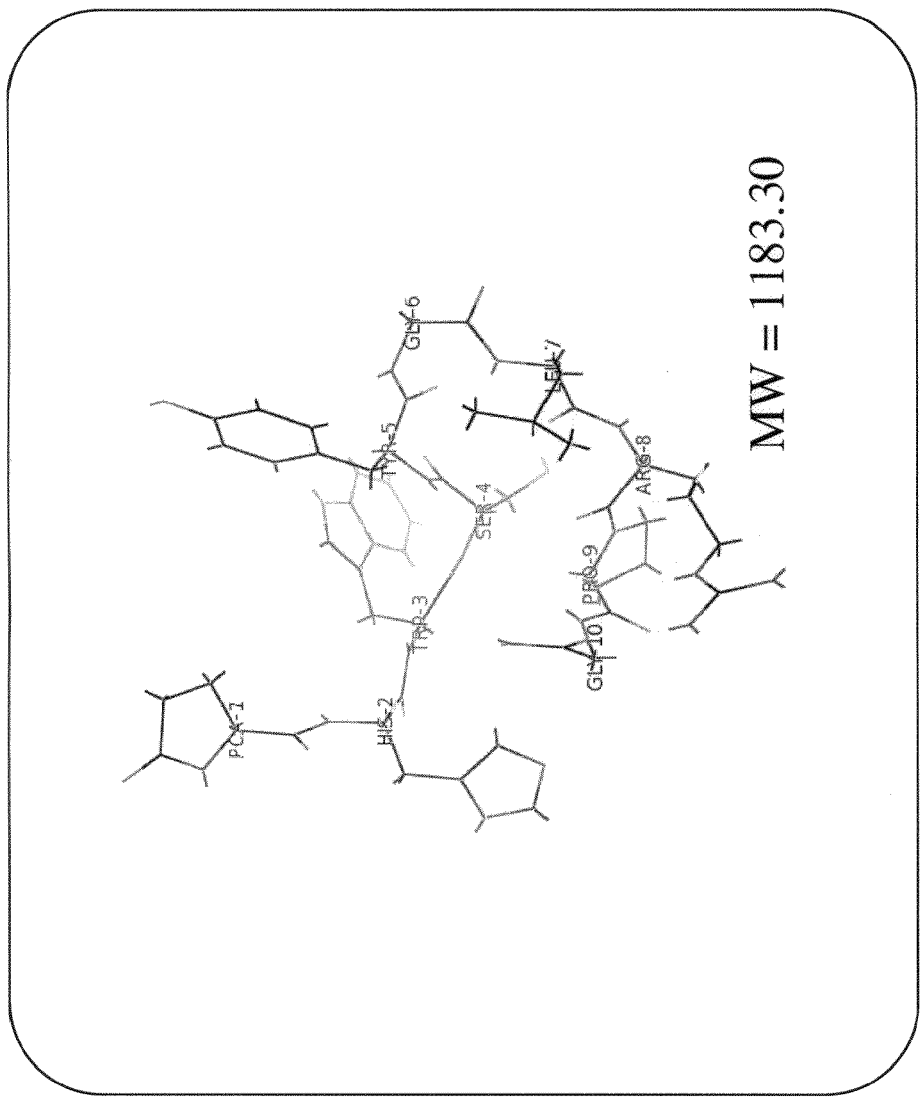

FIG. 1 shows the molecular structure for GnRH (pGlu-His-Trp-Ser-Tyr-Gly-Leu-Arg-Pro-Gly-$NH_2$; SEQ ID NO: 1) in accordance with one embodiment of the present invention.

Figure 2:
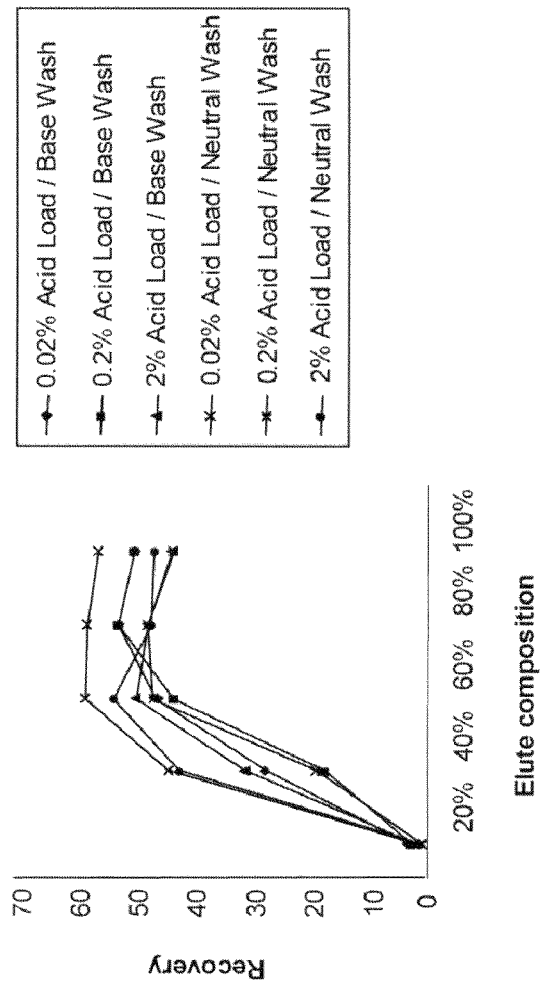

FIG. 2 shows an solid phase extraction (SPE) elution profile for GnRH in accordance with one embodiment of the present invention.

Figure 3:
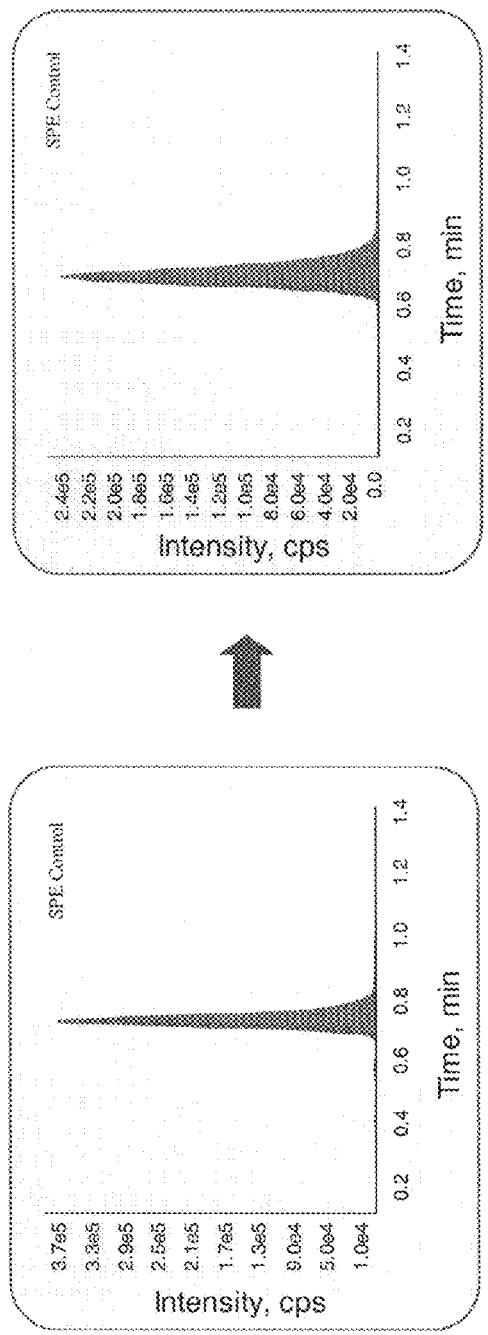
Figure 3:
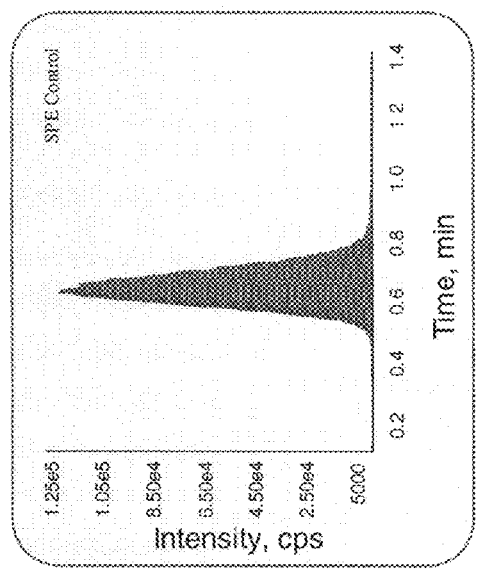

FIG. 3 shows degradation and loss of chromatographic peak shape for GnRH for solid phase extraction (SPE) followed by LC-MS/MS in accordance with one embodiment of the present invention.

Figure 4:
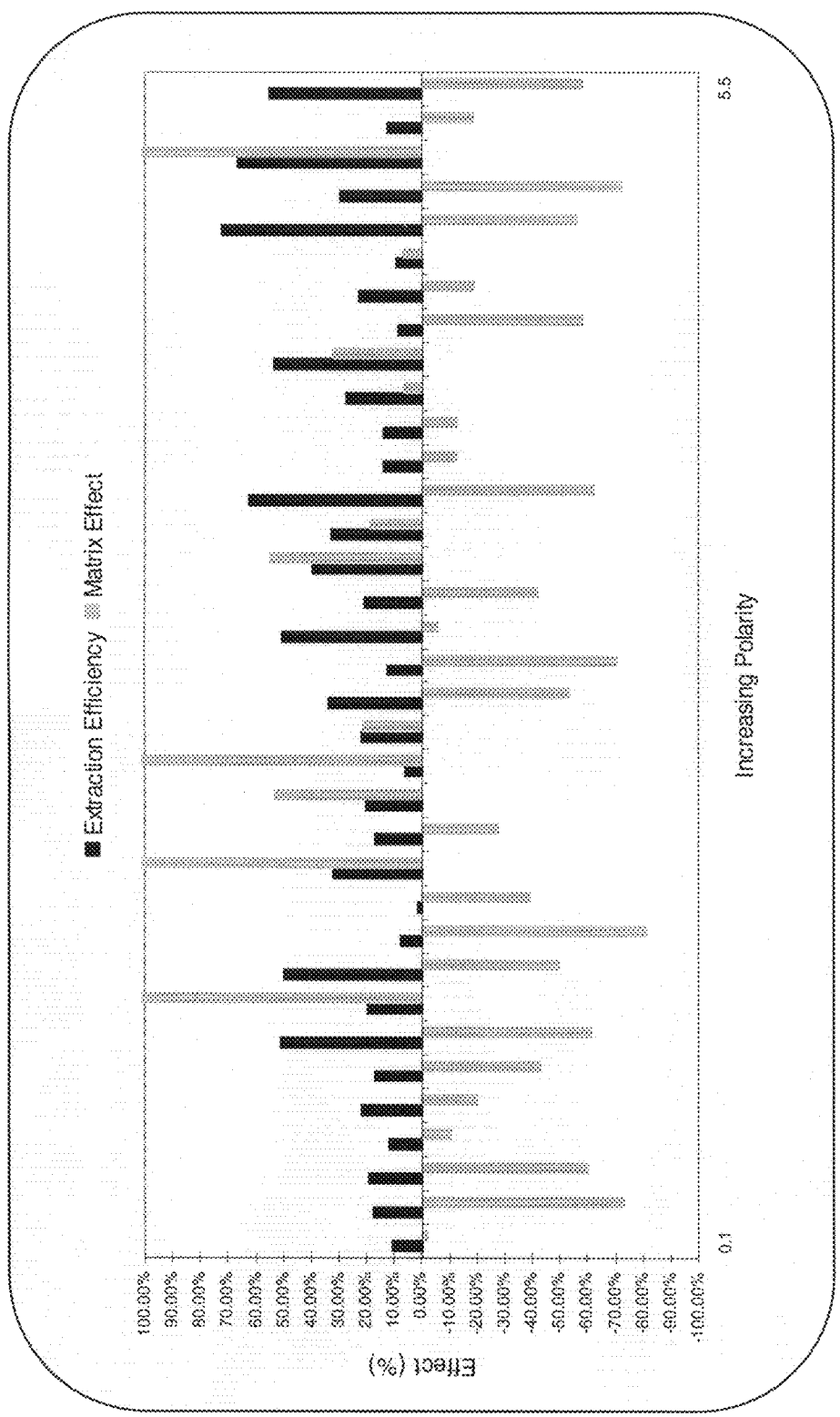

FIG. 4 shows a liquid-liquid extraction (LLE) module for GnRH in accordance with one embodiment of the present invention where high polarity solvents such as methanol and acetonitrile provide extraction of analyte (recovery), together with co-extraction of interfering compounds (matrix effect).

FIG. 5 shows examples of a first dimension reverse phase using two different columns in accordance with alternate embodiments of the present invention where Panel A shows neat GnRH injected into column 1; Panel B shows water injected into column 1; Panel C shows a sample of reconstituted methanol extracted plasma injected into column 1; Paned D shows a sample of reconstituted acetonitrile extracted plasma injected into column 1; Panel E shows neat GnRH injected into column 2; Panel F shows water injected into column 2; Panel G shows a sample of reconstituted methanol extracted plasma injected into column 2; and Paned H shows a sample of reconstituted acetonitrile extracted plasma injected into column 2. Each plot indicates selected reaction monitoring (transitions) for GnRH or the internal standard [(U-23C9, 15N)-Tyr5], [(U-23C6, 15N)-Leu7], [(U-19C5, 15N)-Pro9]-Gonadorelin.

Figure 6A:
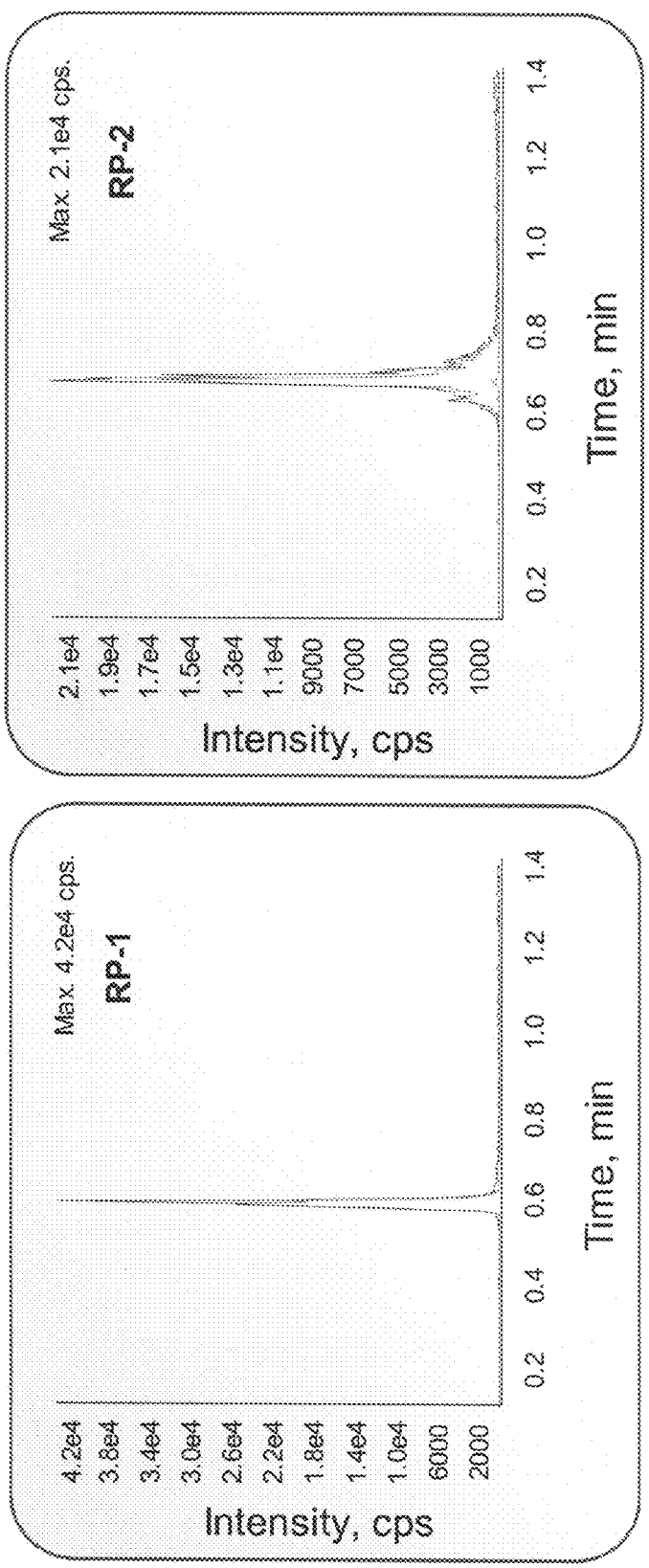

FIG. 6 shows an evaluation of sensitivity in the second dimension three different hydrophilic interaction columns (1, 2 and 3) (Panel 6A) and two different reverse phase columns (1 and 2) (Panel 6B) in accordance with alternate embodiments of the present invention.

Figure 7:
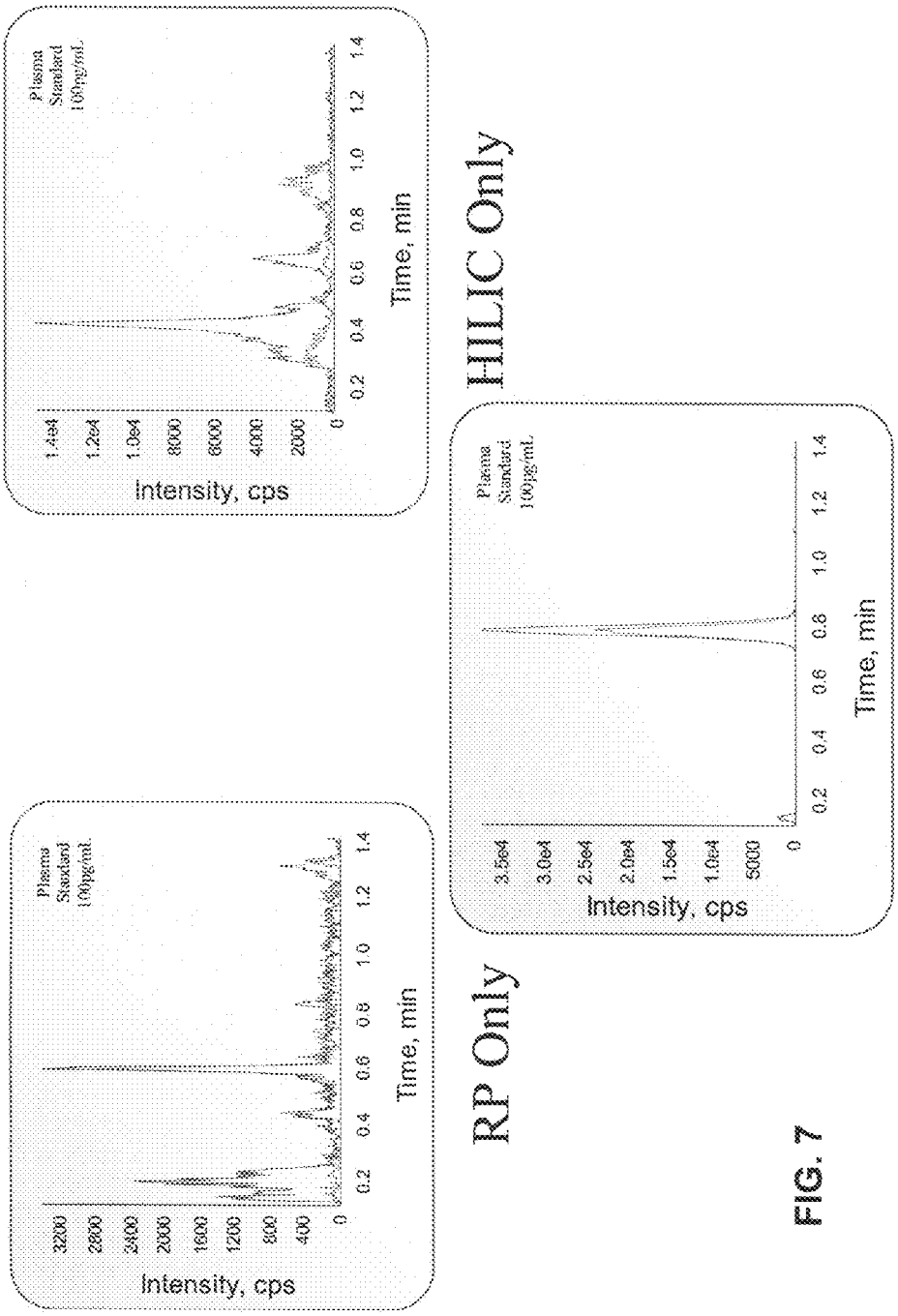

FIG. 7 shows an evaluation of three methods of GnRH purification: reverse phase only (RP only), hydrophilic interaction liquid chromatography only (HILIC only), and reverse phase followed by hydrophilic interaction liquid chromatography (RP-HILIC).

FIG. 8 shows results of the assay for GnRH in accordance with alternate embodiments of the present invention where Panel A shows the LLOQ, Panel B shows the ULOQ, panel C shows a calibration curve, Panel D shows a carryover blank, Panel E shows a patient sample, and panel F shows a cross validation.

FIG. 9 shows results of the assay for GnRH for assay precision and accuracy (Panel A) and for Bias (Panel B) in accordance with alternate embodiments of the present invention.

Figure 10:
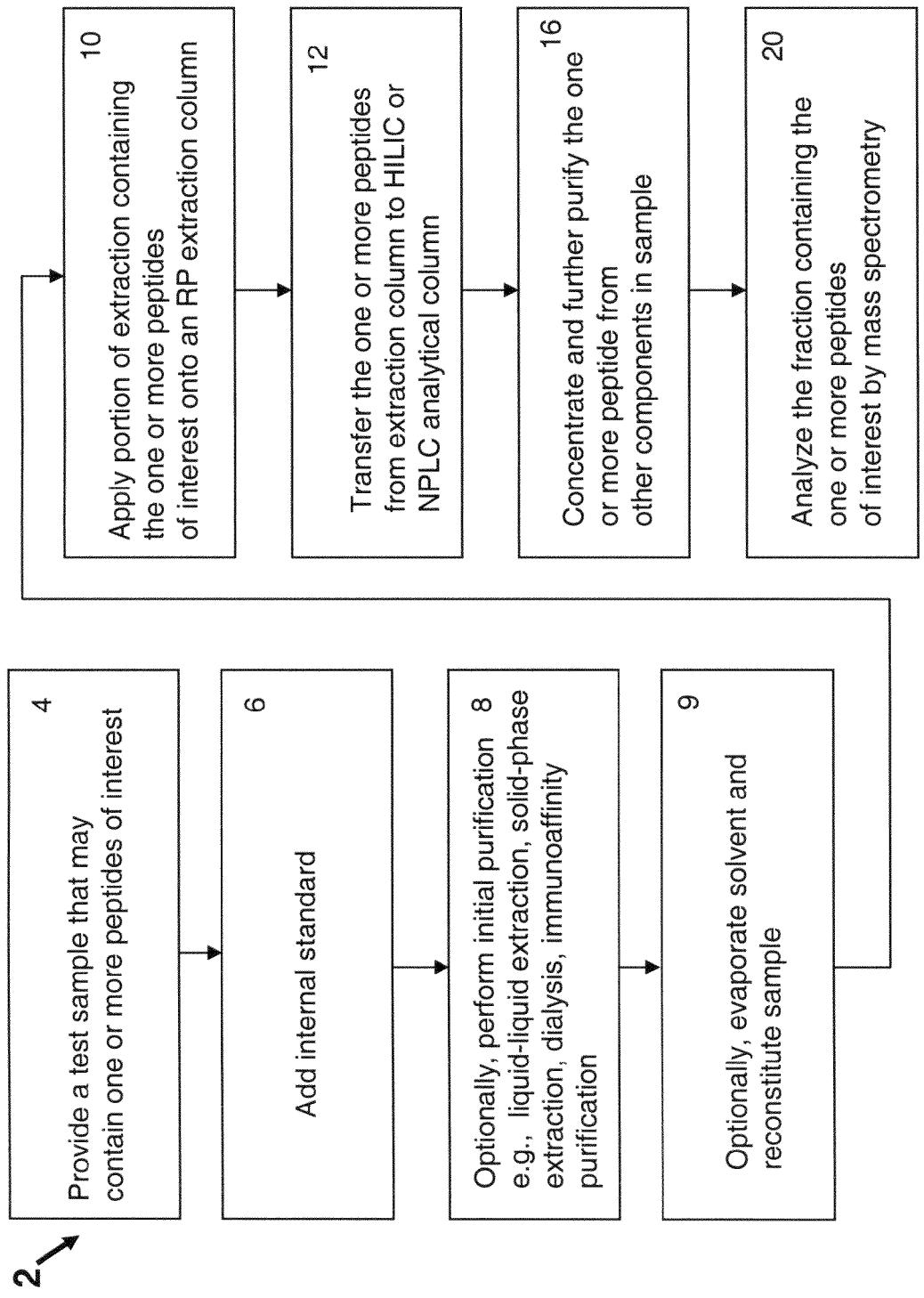

FIG. 10 shows a method for measurement of GnRH in accordance with one embodiment of the present invention.

FIG. 11 shows a system for measurement of GnRH in accordance with one embodiment of the present invention.

Panel A shows a flow diagram for a system according to an embodiment of the present invention. Panel B shows a schematic of a system according to an embodiment of the present invention.

Figure 12:
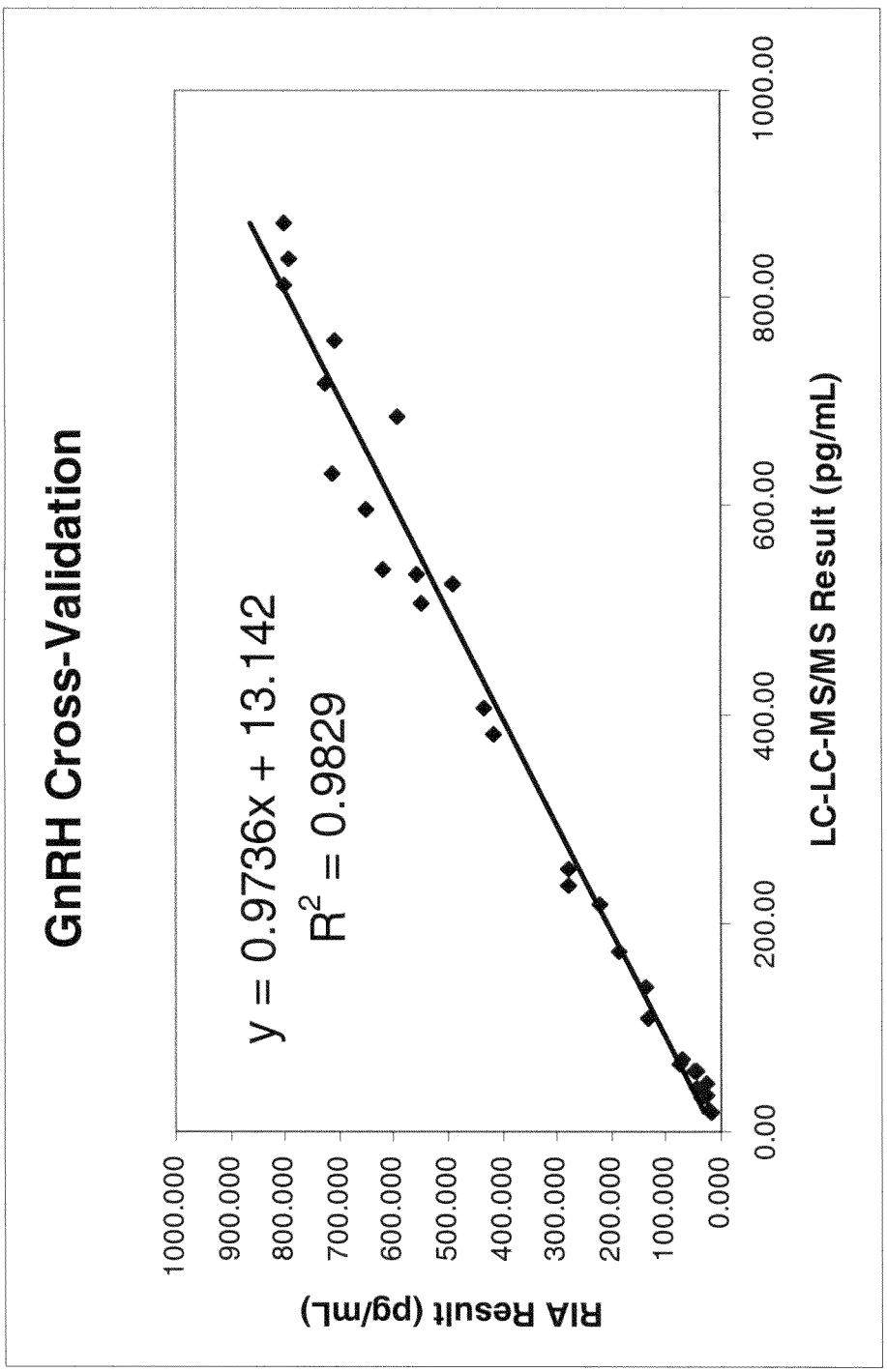

FIG. 12 shows a second experiment showing a cross validation of a sample measured by LC-LC-MS/MS and by RIA in accordance with an embodiment of the present invention.

Figure 13:
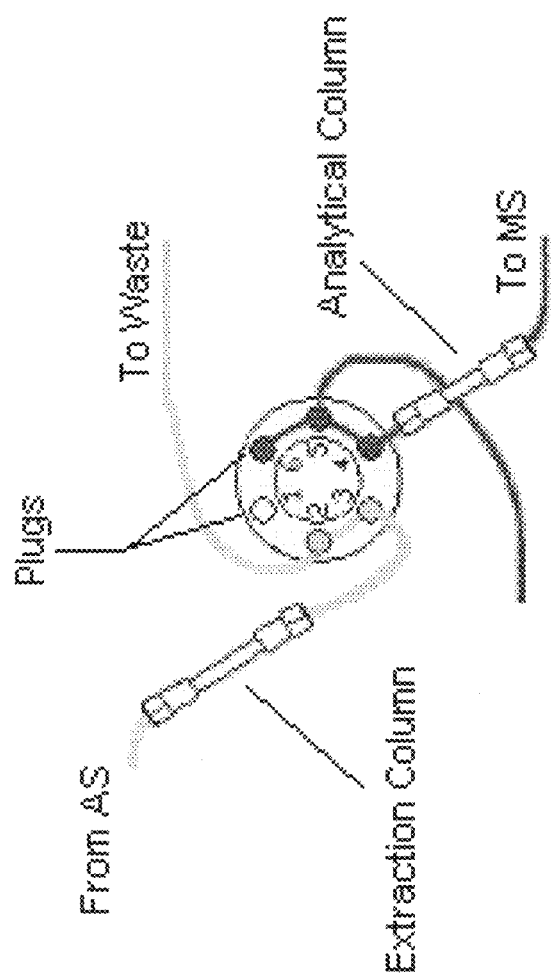

FIG. 13 is a schematic of a LC-LC-MS/MS system in accordance with an embodiment of the present invention.

Figure 14:
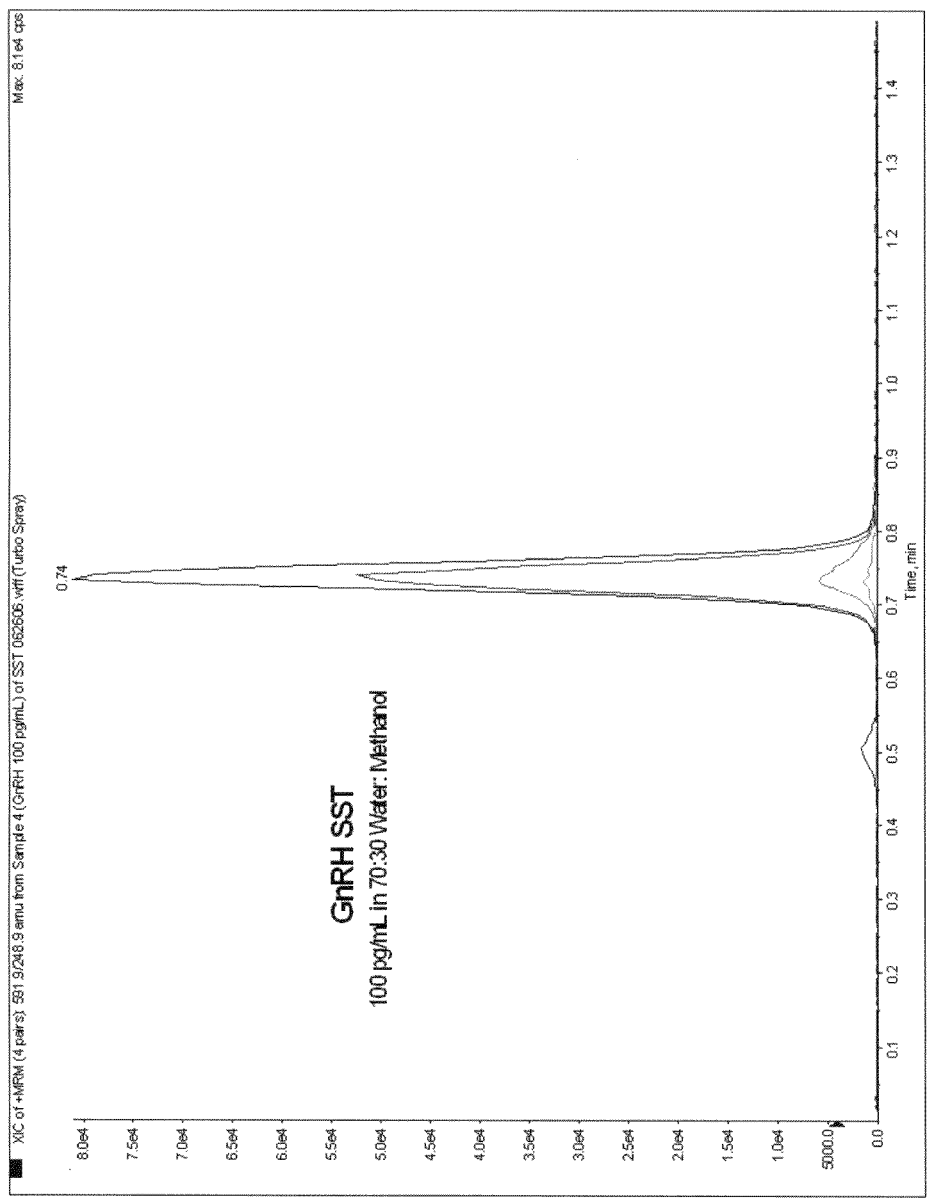

FIG. 14 is a plot of a GnRH system suitability testing chromatogram in accordance with an embodiment of the present invention.

DETAILED DESCRIPTION

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation. The disclosure utilizes the abbreviations shown below.

Abbreviations

APCI=atmospheric pressure chemical ionization
CBP=competitive binding protein
GnRH=Gonadotropin Releasing Hormone
SPE=solid phase extraction
RP=reverse phase
HILIC=hydrophilic interaction liquid chromatography
HPLC=high performance liquid chromatography
LLE=liquid-liquid extraction
LOQ=limits of quantification
LLOQ=lower limit of quantification
IA=immunoassay
ELISA=enzyme linked immunoassay
RIA=radioimmunoassay
SST=system suitability test
ULOQ=upper limit of quantification
2D-LC-MS/MS=two-dimensional liquid chromatography hyphenated to tandem mass spectrometry
(LC)-LC-MS/MS=two-dimensional liquid chromatography tandem hyphenated to tandem mass spectrometry
(LC)-MS/MS=liquid chromatography hyphenated to tandem mass spectrometry Definitions While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

As used herein, the term "biomarker" is any biomolecule that may provide biological information about the physiological state of an organism. In certain embodiments, the presence or absence of the biomarker may be informative. In other embodiments, the level of the biomarker may be informative. A biomarker may be a hormone, such as an endogenous peptide.

"Polypeptide" and "protein" are used interchangeably herein to describe protein molecules that may comprise either partial or full-length proteins. The term "peptide" is used to denote a less than full-length protein or a very short protein unless the context indicates otherwise.

As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid.

Typically, the amino acids making up a protein are numbered in order, starting at the amino terminal residue and increasing in the direction toward the carboxy terminal residue of the protein.

As used herein, the terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the analyte, for example, one or more components that could interfere with detection of an analyte by mass spectrometry.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC), hydrophilic interaction liquid chromatography (HILIC), and normal phase liquid chromatography (NPLC). The terms HILIC and NPLC are used interchangeably and relate to a chromatographic separation whereby the stationary phase is polar in nature (i.e. silica, cyano, amino, and similar types of hydrophilic functionalized packing).

As used herein, the term "HPLC" or "high performance liquid chromatography" refers to liquid chromatography in which the degree of separation is increased by forcing the mobile phase under pressure through a stationary phase, typically a densely packed column.

The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups. The chromatographic column includes an inlet for receiving a sample and an outlet for discharging an effluent that includes the fractionated sample. In the method, the sample (or pre-purified sample) may be applied to the column at the inlet, eluted with a solvent or solvent mixture, and discharged at the outlet. Different solvent modes may be selected for eluting different analytes of interest. For example, liquid chromatography may be performed using a gradient mode, an isocratic mode, or a polytyptic (i.e. mixed) mode.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having a average diameter of less than or equal to 5 µm. In some embodiments, the analytical column is a functionalized silica or polymer-silica hybrid, or a polymeric particle or monolithic silica stationary phase, such as a phenyl-hexyl functionalized analytical column, or a Thermo Cyanopropyl silica (5 um) column, a Thermo Betasil silica (5 um) column, or a Thermo Hypersil (5 um) column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Zorbax Stable Bond (SB) C-18 reverse phase column, or a Thermo Biobasic C-18 column.

The term "heart-cutting" refers to the selection of a region of interest in a chromatogram and subjecting the analytes eluting within that region of interest to a second separation, e.g., a separation in a second dimension.

The term "miniaturized" refers to a separation performed using a reduced system, such as a microchip.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various types of ionization, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various types of ionization, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released. The term "nanospray" refers to a form of electrospray ionization where small droplets (<10 µm) are generated using a miniaturized electrospray emitter or nozzle.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+ (see e.g., Robb et al., 2000, Anal. Chem. 72(15): 3653-3659).

The term "inductively coupled plasma" as used herein refers to methods in which a sample is interacted with a partially ionized gas at a sufficiently high temperature to atomize and ionize most elements.

The term "ionization" and "ionizing" as used herein refers to the process of generating an analyte ion having a net electrical charge. Negative ions are those ions having a net negative charge of one or more electron units, while positive ions are those ions having a net positive charge of one or more units.

The term "desorption" as used herein refers to the removal of an analyte from a surface and/or the entry of an analyte into a gaseous phase.

As used herein, the term "immunoassay" (IA) refers to a method for measuring the amount of an analyte of interest by quantifying the binding, or the inhibition of binding, of a substance to an antibody. Where an enzyme is used to detect the amount of binding of the substance (e.g. antigen) to an antibody, the assay is an enzyme-linked immunoassay (ELISA). As used herein, the term "radioimmunoassay" (RIA) refers to a method for measuring the amount of an analyte of interest by quantifying the binding, or the inhibition, of binding, of a radiolabed substance to an antibody.

As used herein, the term "hemolyzed" refers to the rupturing of the red blood cell membrane, which results in the release of hemoglobin and other cellular contents into the plasma or serum. Also, the term "lipemic" refers to an excess of fats or lipids in a sample.

Analysis of Biomarker Analytes by (LC)-LC-MS/MS

Thus, embodiments of the present invention relate to methods and systems for the quantitative analysis of endogenous analytes such as peptides and/or other types of analytes for clinical diagnosis. The present invention may be embodied in a variety of ways.

In certain embodiments, the present invention comprises a methods and systems for determining the presence or amount of at least one analyte of interest in a sample. In one embodiment, the sample is a biological sample.

For example, in one embodiment, the present invention comprises a method for determining the presence or amount of an analyte in a sample, comprising chromatographically separating the analyte from other components in the sample. The method may further comprise analyzing the chromatographically separated analyte by mass spectrometry to determine the presence or amount of the analyte in the sample. Also, the method may comprise providing a biological sample believed to contain the analyte. For example, in one embodiment, the present invention comprises a method for determining the presence or amount of an analyte in a sample comprising the steps of: (a) providing a sample believed to contain the analyte; (b) chromatographically separating the analyte from other components in the sample using at least one of reverse phase liquid chromatography or hydrophilic interaction liquid chromatography; and (c) analyzing the chromatographically separated analyte by mass spectrometry to determine the presence or amount of the analyte in the sample. In certain embodiments, at least one of the separation and/or measuring steps comprises miniaturized components.

The methods and systems of the present invention may be used to measure analytes that are small polar molecules such as peptides, polypeptides and proteins, as well as other types of molecules that comprise polar groups such that the analyte is more soluble in a polar solvent than a non-polar solvent. In certain embodiments, the analyte has a plurality of residues of opposite charge such that the analyte has polarity at neutral pH. In certain embodiments, the molecules are small (e.g., <100 Daltons). As used herein, a polar solvent is a solvent in which the molecules have a large permanent electric dipole. Examples of polar solvents include water, methanol and acetonitrile.

In certain embodiments, the chromatography may comprise high performance liquid chromatography (HPLC). The type of HPLC may depend on the bioanalyte. In some embodiments, the chromatography may comprise reverse phase liquid chromatography as an extraction chromatography used for a first dimension separation. Additionally or alternatively, the chromatography may comprise hydrophilic interaction liquid chromatography (HILIC) or normal phase liquid chromatography (NPLC) as an analytical liquid chromatography used for a second dimension separation. For example, the chromatography separation may comprise RP extraction chromatography followed by HILIC analytical chromatography. This approach may, in certain embodiments, be well-suited to the analysis of highly charged biomolecules, as for example, polar peptides, such as GnRH. Or, in some embodiments, depending on the type of purification step used prior to chromatography, HILIC or NPLC may be used without RPLC.

For example, in certain embodiments, the step of chromatographically separating the analyte from other components in the sample comprises the steps of: (i) applying at least a portion of the sample comprising the analyte to a reverse phase liquid chromatography extraction column; (ii) eluting at least a portion of the analyte from the reverse phase column; (iii) applying at least a portion of the analyte eluted from the reverse phase liquid chromatography extraction column onto a hydrophilic interaction liquid chromatography analytical column; and (iv) eluting at least a portion of the analyte from the hydrophilic interaction liquid chromatography analytical column.

In an embodiment, the method may comprise purifying the analyte of interest prior to chromatography. In certain embodiments, the method may comprise partially purifying the analyte from other components in the sample prior to the step of chromatographically separating the analyte from other components in the sample.

For example, the sample may be partially purified by liquid-liquid extraction (LLE) and/or solid-phase extraction (SPE). In yet another embodiment, the purification step may comprise use of an antibody to the peptide and/or protein. The antibody may be attached to a solid phase such as a bead. Or, the purification may comprise dialysis of the sample to separate a peptide that is bound to proteins from peptide that is free in solution as further described herein. Alternatively, the method may comprise the step of diluting the sample into a solvent or solvents used for LC and/or MS/MS such that proteins in the sample precipitate. In certain embodiments, the step of partially purifying the analyte from other components in the sample prior to chromatographic separation comprises at least one of: (i) liquid-liquid extraction; (ii) solid-phase extraction; (iii) dialysis to separate a population of analyte molecules that are not bound to proteins from a population of analyte molecules that are protein-bound; (iv) binding of the analyte to an antibody that recognizes the analyte as an antigen; or (v) diluting a portion of the analyte into a solvent.

Thus, in some embodiments, the method may comprise the use of liquid-liquid extraction (LLE) with two liquid chromatography steps. For example, where the analyte is the peptide GnRH, LLE with acetonitrile may be used. For example, in certain embodiments, the method for determining the presence or amount of one or more analytes in a test sample may comprise the steps of: (a) providing a sample suspected of containing one or more analytes of interest; (b) optionally, partially purifying the analyte from other components in the sample by at least one of liquid-liquid extraction, sample dilution into a solvent to precipitate protein, solid phase extraction, antibody purification, or dialysis; (c) transferring the extracted analyte onto a reverse phase extraction column (i.e., on-line or off-line); (d) transferring the analyte from the extraction column onto a HILIC or NPLC analytical column and chromatographically separating the analyte from other components in the sample; and (e) analyzing the chromatographically separated analyte by mass spectrometry to determine the presence or amount of the analyte in the test sample.

In alternate embodiments, HILIC or NPLC increases sensitivity at least 5-fold, or at least 10-fold, or at least 12-fold, or at least 20-fold, or at least 50-fold. This increase may be seen where HILIC or NPLC is used for analysis of polar biomolecules. For example, this increase may be seen where HILIC or NPLC is used for analysis of singly or multiply charged analytes, such as peptides, polypeptides, proteins or other small (e.g., <1,000 Daltons) molecules.

In other embodiments, the present invention comprises a system for determining the presence or amount of one or more analytes of interest in a sample. In an embodiment, the system comprise a station for chromatographically separating the analyte from other components in the sample. In certain embodiments, the station for chromatographically separating the analyte from other components in the sample may comprise at least one of a reverse phase liquid chromatography column or a hydrophilic interaction liquid chromatography column. The system may also comprise a station for analyzing the chromatographically separated analyte by mass spectrometry to determine the presence or amount of the analyte in the sample. Also, the system may comprise a station for providing a sample believed to contain the analyte. For example, in certain embodiments, the present invention may comprise a system for determining the presence or amount of an analyte in a sample, the system comprising: a station for providing a sample believed to contain the analyte; a station for chromatographically separating the analyte from other components in the sample, the station comprising at least one of a reverse phase liquid chromatography column or a hydrophilic interaction liquid chromatography column; and a station for analyzing the chromatographically separated analyte by mass spectrometry to determine the presence or amount of the analyte in the test sample.

In some embodiments, the system may also comprise a station for partially purifying the analyte from other components in the sample. For example, the system may comprise a station for partially purifying the analyte from other components in the sample prior to chromatographic separation of the analyte from other components in the sample. In certain embodiments, the station for partially purifying the analyte comprises at least one of: (i) a station for liquid-liquid extraction; (ii) a station for solid-phase extraction; (iii) a station for dialyzing a plurality of samples to separate a population of analyte molecules that are not bound to proteins from a population of analyte molecules that are protein-bound; (iv) a station for performing an antibody-based purification of the analyte; or (v) a station for diluting a portion of the analyte into a solvent such that proteins in the sample precipitate Also in certain embodiments, at least one of the stations is automated and/or controlled by a computer. For example, as described herein, in certain embodiments, at least some of the steps are automated such that little to no manual intervention is required. Also, in certain embodiments, at least on of the stations comprises components that are miniaturized.

In one embodiment, the station for chromatographic separation comprises at least one apparatus to perform liquid chromatography (LC). In one embodiment, the station for liquid chromatography comprises a column for reverse phase extraction chromatography. Additionally or alternatively, the station for liquid chromatography comprises a column for hydrophilic interaction liquid chromatography (HILIC) or normal phase liquid chromatography NPLC. In one embodiment, the station for liquid chromatography comprises a reverse phase liquid chromatography extraction column and a hydrophilic interaction liquid chromatography analytical column. The HILIC or NPLC may be used as an analytical chromatography step. In certain embodiments, the column for extraction chromatography and/or analytical chromatography comprise a single station. For example, in one embodiment, liquid chromatography is used to purify the analyte of interest from other components in the sample that co-purify with the analyte of interest after extraction or dilution of the sample. In certain embodiments, the separation is performed in miniature on a microchip platform, either on-line or off-line.

The system may also include a station for analyzing the chromatographically separated one or more analytes of interest by mass spectrometry to determine the presence or amount of the one or more analytes in the test sample. In certain embodiments, the station comprises an electrospray and/or nanospray ion source. In certain embodiments, tandem mass spectrometry is used (MS/MS). For example, in certain embodiments, the station for tandem mass spectrometry comprises an Applied Biosystems API4000 or API5000 or thermo quantum or Agilent 7000 triple quadrupole mass spectrometer.

The system may also comprise a station for extracting the one or more analytes from the test sample and/or diluting the sample. In an embodiment, the station for extraction comprises a station for liquid-liquid extraction. The station for liquid-liquid extraction may comprise equipment and reagents for addition of solvents to the sample and removal of waste fractions. In some cases, an isotopically-labeled internal standard is used to standardize losses of the analyte that may occur during the procedures. Thus, the station for liquid-liquid extraction may comprise a hood or other safety features required for working with solvents.

Additionally or alternatively, the system may comprise as station for solid-phase extraction. Generally, solid phase extraction is an extraction method that uses a solid phase and a liquid phase to isolate one, or one type, of analyte from a solution. Thus, the station for solid-phase extraction may comprise a column or other type of container that is filled with the solid phase, a dispenser to apply the sample to the solid phase, and a solvent that is used to elute the analyte from the solid phase.

Additionally, the system may comprise a station for immunoaffinity purification of the bioanalyte and/or dialysis of the sample as described in more detail herein.

A variety of mass spectrometry techniques may be used to measure and quantify the analyte in the methods and systems of the present invention. In certain embodiments, the mass spectrometry comprises tandem mass spectrometry. Also in certain embodiments, the mass spectrometry is at least one of electrospray mass spectrometry or nanospray mass spectrometry. Or other types of mass spectrometry described herein may be used.

In some embodiments, the analyte used in the methods and systems of the present invention is polar in that it has a net charge a neutral pH. In certain embodiments, the analyte is at least one of a peptide, a polypeptide, or a protein. Thus, in certain embodiments, the analyte is a peptide that comprises a plurality of polar residues such that the peptide is polar. For example, the analyte may be an endogenous protein and/or peptide in a human subject.

For example, in one embodiment, the analyte is GnRH peptide of SEQ ID NO: 1. Or, other highly charged peptides may be separated using the methods and systems of the present invention. In the embodiment where GnRH is being monitored, the method may comprise ionizing the GnRH to produce one or more GnRH ions detectable by mass spectrometry having a mass/charge ratio comprising at least one of 591.9, 248.9, or 220.9. Where a radiolabeled standard for GnRH is used, the method may further comprise ionizing the radiolabled GnRH to produce one or more GnRH ions detectable by mass spectrometry having a mass/charge ratio comprising at least one of 603.1, 249.1, or 178.0. Thus, in one embodiment the present invention comprise a method for determining the presence or amount of an GnRH in a sample comprising the steps of: (a) providing a sample believed to contain GnRH; (b) chromatographically separating the GnRH from other components in the sample using reverse phase liquid chromatography and hydrophilic interaction liquid chromatography; and (c) analyzing the chromatographically separated GnRH by mass spectrometry to determine the presence or amount of the analyte in the sample.

For example, in certain embodiments of the methods and systems of the present invention the step of analyzing the GnRH by mass spectrometry comprises ionizing the chromatographically separated GnRH to produce one or more GnRH ions having a mass/charge ratio comprising at least one of a parent ion of $591.9\pm0.5$, or a daughter ion of $248.9\pm0.5$, or $220.9\pm0.5$ and detecting the ions by mass spectrometry, wherein the presence or amount of the GnRH ions is related to the presence or amount of GnRH in the sample. Also, in certain embodiments of the methods and systems of the present invention the presence or amount of GnRH ion is related to the presence or amount of GnRH in the sample by comparison to a reference standard. For example, the reference standard may comprise $[(U-^{23}C_9, ^{15}N)-Tyr^5]$, $[(U-^{23}C_6, ^{15}N)-Leu^7]$, $[(U-^{19}C_5, ^{15}N)-Pro^9]$-Gonadorelin. Where the reference standard is $[(U-^{23}C_9, ^{15}N)-Tyr^5]$, $[(U-^{23}C_6, ^{15}N)-Leu^7]$, $[(U-^{19}C_5, ^{15}N)-Pro^9]$-Gonadorelin, the reference standard may be detected by ionizing the reference standard to produce one or more reference ions having a mass/charge ratio comprising at least one of a parent ion of $603.1\pm0.5$, or a daughter ion of $249.1\pm0.5$ or $178.0\pm0.5$, and detecting the ions by mass spectrometry, wherein the presence or amount of the reference ions is related to the presence or amount of reference standard.

The methods and systems of the present invention allow for sensitive and accurate measurement of analytes. In an embodiment, at least one of the components used in the methods and/or systems of the present invention is miniaturized. The use of RPLC and HILIC may, in certain embodiments, provide increased sensitivity. In alternate embodiments, the use of the hydrophilic interaction liquid chromatography column in the methods and systems of the present invention provides an increase in sensitivity of between about 5 to 12 fold, or between 5 to 20 fold, or between 5-50 fold for detection of the analyte as compared to using only the reverse phase liquid chromatography extraction column. For example, in one embodiment, the measurement comprises a lower limit of quantitation for GnRH peptide of about 10 pg/mL. Also in some embodiments, the measurement comprises an upper limit of quantitation for GnRH of about 1000 pg/mL.

In certain embodiments, the test samples suitable for analysis by the methods and systems of the present invention can include any liquid sample that can contain one or more target analytes of interest. In an embodiment, the analyte is endogenous to a subject. For example, in some embodiments, the test sample comprises a biological sample. As used herein, the term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample.

As used herein, a subject may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. The human subject may comprise, in alternate embodiments, an adult, a child, or an infant. In some embodiments, the subject is a patient, that is, a living person presenting themselves in a clinical setting for diagnosis, prognosis, or treatment of a disease or condition. In some embodiments, the test sample is not a biological sample, but comprises a non-biological sample, e.g., obtained during the manufacture or laboratory analysis of a synthetic compound, such as a modified peptide or a steroid, which can be analyzed to determine the composition and/or yield of the manufacturing and/or analysis process.

As described herein, the methods and systems of the present invention may be used to measure analytes that are small polar molecules such as peptides, polypeptides and proteins, as well as other types of molecules that comprise polar groups such that the analyte is more soluble in a polar solvent than a non-polar solvent. In certain embodiments, the analyte has a plurality of residues of opposite charge such that the analyte has polarity at neutral pH.

Examples of such polar analytes include many proteins, sugars, oligosaccharides, nucleotide molecules, some vitamins (e.g., vitamin C and other water soluble vitamins) and the like. Examples of proteins that may be isolated may include antibodies or portions thereof, antibody epitopes, enzymes (e.g., peptidases, lipases, nucleases, catalases), lectins, extracellular matrix proteins (fibrin, elastin, laminin, fibronectin), growth factors (e.g., transforming growth factor, nerve growth factors, fibroblast growth factors, platelet-derived growth factors, and the like), cancer-derived polypeptides (e.g., cancer antigens), oncogene proteins, bioactive proteins (e.g., calmodulin) and the like.

In some embodiments, the methods may be used to measure and/or quantify peptides or polypeptides. Such peptides or polypeptides may include hormones such as, but not limited to hypothalamic hormones and hypophysiotropic hormones, anterior, intermediate and posterior pituitary hormones, pancreatic islet hormones, hormones made in the gastrointestinal system, renal hormones, thymic hormones, parathyroid hormones, adrenal cortical and medullary hormones. Also, the methods and systems may measure peptides that are neurotransmitters or that act as growth factors.

Example peptides, polypeptides and/or proteins that may be detected and quantified by the methods and systems of the present invention may include at least the following polypeptides, fragments thereof, and modified polypeptides derived from these polypeptides: adrenomedullin, amyloid-beta protein, humanin, angiotensin-I, angiotensin-II, bactenecin, dermaseptins, melittin, erythromycin resistance peptide, keotlide resistance peptide, corticotropin-releasing factor, follicle-stimulating-hormone-releasing factor, gonadotropin-releasing factor, lutenizing hormone-releasing factor, melanotropin-releasing factors, prolactin-releasing factor, prolactin release-inhibiting factor, somatotropin-releasing factor, growth hormone-releasing factor, somatotropin release-inhibiting factor, thyrotropin-releasing factor, chorionic gonadotropin, chorionic somatomammotropin, adrenocorticotropic hormone, Ocytocin, [Ser$^4$,Gln$^8$]ocytocin, [Ser$^4$,Ile$^8$]ocytocin, [Ile$^8$]ocytocin, [Arg$^8$]ocytocin, lipotropic hormone, luteinizing hormone, interstitial cell-stimulating hormone, melanocyte-stimulating hormone, mammatropic hormone, mammatropin, lactotropic hormone, lactotropin, somatropic hormone, growth hormone, thyrotropic hormone, menopausal gonadotropin, antidiuretic hormone, kinin-9, kinin-10, cholecystokinin, thyrocalcitonin, gastrin II, hyperglycemic factor, parathyroid hormone, parathormone, sulfation factor, thymin, apelin, atriopeptin I and III, bombesin, urodilatin, gastrin releasing peptide, bradykinin, gastrin I, enterostatin, galanin, glucagon, insulin, proinsulin, C protein, insulin-like growth factor 1, insulin-like growth factor 2, insulin like growth factor binding peptides 1, 2 and 3, ghreiln, oxrexin, glycogenolysis-inhibiting peptide, extendin, insulin receptor, glucagon-like peptide, motillin, panacreastatin, peptide Y, peptide YY, sorbin, secretin, helodermin, calcitonin, calcitonin-related peptides, intermedin, human hypercalcemia malignancy factor, human parathyroid hormone related protein, carcinoma antigen peptide, viral peptides (e.g., peptides derived from HIV, influenza, hepatitis A, B, or C), melanoma associated antigen, melanotcyte protein, fibrinogen-binding peptide, lamin A and B peptides, type I procollagen, vitronectin, myelin basic protein, myelin proteolipid protein, endothelin-I, endothelin-II, endothelin-III, sarafotoxin, vasoactive intestinal peptide, vasoactive intestinal contractor, ghrelin, obstatin, epidermal growth factor, fibroblast growth factor, fibroblast growth factor antagonist, insulin like growth factor, keratinocyte growth factor, platelet-derived growth factor, CCK releasing factor, sauvagine, urocortin, prolactin releasing peptide, somatostatin, edoterotide, urotensin II, melanotan II, alpha-MSH, beta-MSH, gamma-MSH, adipokinetic hormone II, brain injury-derived neurotrophic peptide, buccalin, coritstatin, octaneuropeptide, neuropeptide FF, neuropeptide W-30, neuropeptide W-23, neuropeptide Y, nociceptin, nocistatin, orexin A, orexin B, secretoneurin, neurotensin, deltorphin, leu-enkephalin, met-enkephalin, beta-endorphin, vasopressin, oxytocin, vasotocin, myelin basic protein, protein kinase C, substance P, pepstatin, bradykinin, cholecystokin, gastrin, secretin, somatostatin, prolactin, galanin, dynorphin, motilin, thyrotropin, leuteinizing hormone, vasopressin, and thyrotropin releasing peptide.

A variety of methods may be used to extract the analyte of interest from the sample. In certain embodiments, extracting the biomarker or analyte from the test sample comprises at least one of a liquid-liquid extraction procedure, a solid-phase extraction procedure, immunoaffinity purification and/or dialysis. For example, for the analysis of GnRH, acetonitrile or a similar solvent may be used for extraction of the peptide from plasma.

In certain embodiments, purifying the at least one analyte of interest from the test sample may also comprise the use of a liquid chromatography extraction column. In one embodiment, the column is on-line. In an embodiment, purification of the analyte of interest using a extraction column may comprises the steps of: (i) transferring the test sample to a reverse phase extraction column; and (ii) eluting the analyte of interest from the extraction column.

In certain embodiments, the methods and systems of the present invention may comprise multiple liquid chromatography steps. Thus, in certain embodiments, a two-dimensional liquid chromatography (LC) procedure is used. For example, in certain embodiments, the method and systems of the present invention may comprise transferring the analyte of interest from the reverse phase LC extraction column to a hydrophilic interaction LC (HILIC) analytical column. In one embodiment, transferring the analyte from the extraction column to an analytical column is done by a heart-cutting technique. In another embodiment, the analyte is transferred from the extraction column to an analytical column by a chromatofocusing technique. Alternatively, the analyte is transferred from the extraction column to an analytical column by a column switching technique. These transfer steps may be done manually, or may be part of an on-line automated system.

Various columns comprising stationary phases and mobile phases that may be used for extraction or analytical liquid chromatography are described herein; alternatives may be used as is known by those skilled in the art. The column used for extraction liquid chromatography may be varied depending on the analyte of interest. In some embodiments, the extraction column is a functionalized silica or polymer-silica hybrid or polymeric particle or monolithic silica stationary phase, such as a Zorbax Stable Bond (SB) C-18 reverse phase column, or a Thermo Biobasic C-18 column. The column used for analytical liquid chromatography may be varied depending on the analyte of interest and/or the column that was used for the extraction liquid chromatography step. For example, in certain embodiments, the analytical column comprises particles having an average diameter of less than or equal to about 5 μm. In some embodiments, the analytical column is a functionalized silica or polymer-silica hybrid, or a polymeric particle or monolithic silica stationary phase, such as a Thermo Cyanopropyl silica (e.g., 50 mm×2.1 mm; 5 um) column, a Thermo Betasil silica (e.g., 50 mm×2.1 mm; 5 um) column, or a Thermo Hypersil silica (e.g., 50 mm×2.1 mm; 5 um) column.

A variety of methods may be used to quantify the analyte of interest once the analyte has been substantially purified (i.e., substantially separated away from other components that may have been present in the sample). In some embodiments, mass spectrometry is used to quantify the analyte present in the sample. In certain embodiments, the mass spectrometer may comprise a tandem mass spectrometer (MS/MS). For example, in one embodiment of the methods and systems of the present invention, the tandem MS/MS spectrometry comprises a triple quadrupole tandem mass spectrometer.

The tandem MS/MS may be operated in a variety of modes. In one embodiment, the tandem MS/MS spectrometer is operated in an positive or negative ion electrospray (ESI) mode. In another embodiment, the system is operated with a nanospray emitter. In some embodiments, the quantification of the analytes and internal standards is performed in the selected reaction monitoring mode (SRM).

Thus, embodiments of the present invention comprise methods and systems for applying liquid chromatography and mass spectrometry as a means to separate an an analyte of interest from other components that may be present in a biological sample. In certain embodiments, two liquid chromatography (LC) steps are used in tandem. Also, the method may comprise an off-line liquid-liquid extraction and/or sample dialysis step as a means to partially purify the sample prior to liquid chromatography. Or, antibody-based purification may be used.

In other embodiments, no partial purification is performed, and the sample is diluted into a solvent or solvents used for LC and/or MS.

The systems and methods of the present invention may, in certain embodiments, provide for a multiplexed assay. For example, certain embodiments of the present invention may comprise a multiplexed liquid chromatography tandem mass spectrometry (LC-MS/MS) or two-dimensional or tandem liquid chromatography-tandem mass spectrometry (LC)-LC-MS/MS) methods for the quantitative analysis of one or more analytes, including proteins or peptides, such as GnRH in biological samples.

Two Dimensional Reverse Phase/Hydrophilic Interaction LC-LC-MS/MS Analysis of GnRH Peptide Thus, embodiments of the present invention comprise an ultra-sensitive LC-LC-MS/MS method for plasma quantification of an analyte. In certain embodiments, the analyte is the endogenous decapeptide, Gonadotropin Releasing Hormone (GnRH). In an embodiment, utilizing buffered solvents with reverse-phase (RP) chromatography may enhance selectivity by eliminating the presence of matrix interferences, but can result in less than acceptable sensitivity. However, the addition of hydrophilic interaction liquid chromatography (HILIC) in the second-dimension can lead to 10-fold or greater sensitivity gains and even greater selectivity.

The molecular structure of GnRH is shown in FIG. 1. The amino acid sequence of GnRH is pGlu-His-Trp-Ser-Tyr-Gly-Leu-Arg-Pro-Gly-NH$_2$ (SEQ ID NO: 1). GnRH is highly polar, with an N-terminal pyroglutamic acid and a C-terminal amide.

The high polarity of the GnRH molecule can make plasma extraction and separation of such peptides from other biomolecules difficult. For example, as shown in FIG. 2, solid-phase extraction (SPE) may result in acceptable yield, but can exacerbate chromatography issues in that peaks are not well defined (FIG. 3). Plasma liquid-liquid extraction (LLE) with non-polar organic solvents may result in low recovery and a high matrix effect (FIG. 4), thus resulting in poor sensitivity.

Thus, experiments were performed to determine a method for improving both sensitivity and selectivity. As discussed in detail below, it was found that sufficient recovery can be achieved with protein precipitation (ppt) using acetonitrile, however, other potentially interfering substances were simultaneously extracted. Utilizing buffered solvents with reverse-phase (RP) chromatography enhanced selectivity by eliminating the presence of matrix interferences, but resulted in poor sensitivity. Hydrophilic interaction liquid chromatography (HILIC) in the second-dimension led to ~10-fold sensitivity gains and even greater selectivity due at least in part to improvement in solvent properties of the samples (i.e., use of solvents that are more organic) as such solvents may have better efficiency when used for electrospray MS analysis.

SPE and LLE Evaluation

As shown in FIG. 2, SPE followed by LC-MS/MS analysis may result in average recoveries between 50% and 60%, however, the reconstituted sample chemistry can quickly lead to column degradation and loss of chromatographic peak shape (FIG. 3).

Liquid-liquid extraction (LLE) with LC-MS/MS analysis may yield poor recovery at lower polarities and high matrix effect throughout the polarity range from heptane (nonpolar) to acetonitrile (polar) (FIG. 4). In FIG. 4, analyte detection is shown by the dark bars, and matrix enhancement or reduction of signal is shown by the lighter bars. Higher polarity extraction solvents (methanol and acetonitrile) gave extraction efficiencies similar to SPE. Thus, it was determined that alternative methods for the reduction of matrix interferences needed to be explored.

First Dimension Post-Column Infusion (Reverse Phase)

Post-column infusion of GnRH was performed in order to evaluate the plasma matrix effect(s). The results of these experiments were used to identify a reverse-phase column that could resolve interfering matrix components from GnRH. These experiments also helped determine a protein precipitation solvent (i.e., in certain embodiments, the solvents used for liquid-liquid extraction will precipitate protein as well as extract the analyte) that extracted the least amount of potentially interfering substances. The results from these experiments were used to maximize ionization efficiency and selectivity. The first dimension (1D) reverse-phase column was selected based on the column's ability to separate GnRH from the potentially interfering substances. The protein precipitation solvent was selected based on the amount of interferences excluded during extraction, as well as, extraction efficiency.

In certain embodiments, certain solvents are preferred for elution of GnRH from a RP column. The results for this type of experiment using two different reverse-phase columns are shown in FIG. 5. FIG. 5A-5D shows the results with a Zorbax Stable Bond (SB) C-18 (50×2.1 mm, 5 µm) reverse phase column (RP Column 1), and FIGS. 5E-5H shows results for a Thermo Biobasic C-18 column (50×2.1 mm, 5 µm) (RP Column 2). The overlapping two plots as shown in each of FIGS. 5A-5H are separate transitions for GnRH as the same precursor molecule (m/z: 591.9) is fragmenting to two product ions: 248.9 and 220.9. Also shown is the transition for the labeled internal standard: 603.1/249.1 and 603.1/178.0 (i.e., plots having about 1/10 intensity as the two plots for the GnRH analyte in FIGS. 5-6). These separate transitions may be used as an internal control to validate that the compound for which the spectrum is being taken is the correct analyte (i.e., GnRH) being monitored.

Figure 5E:
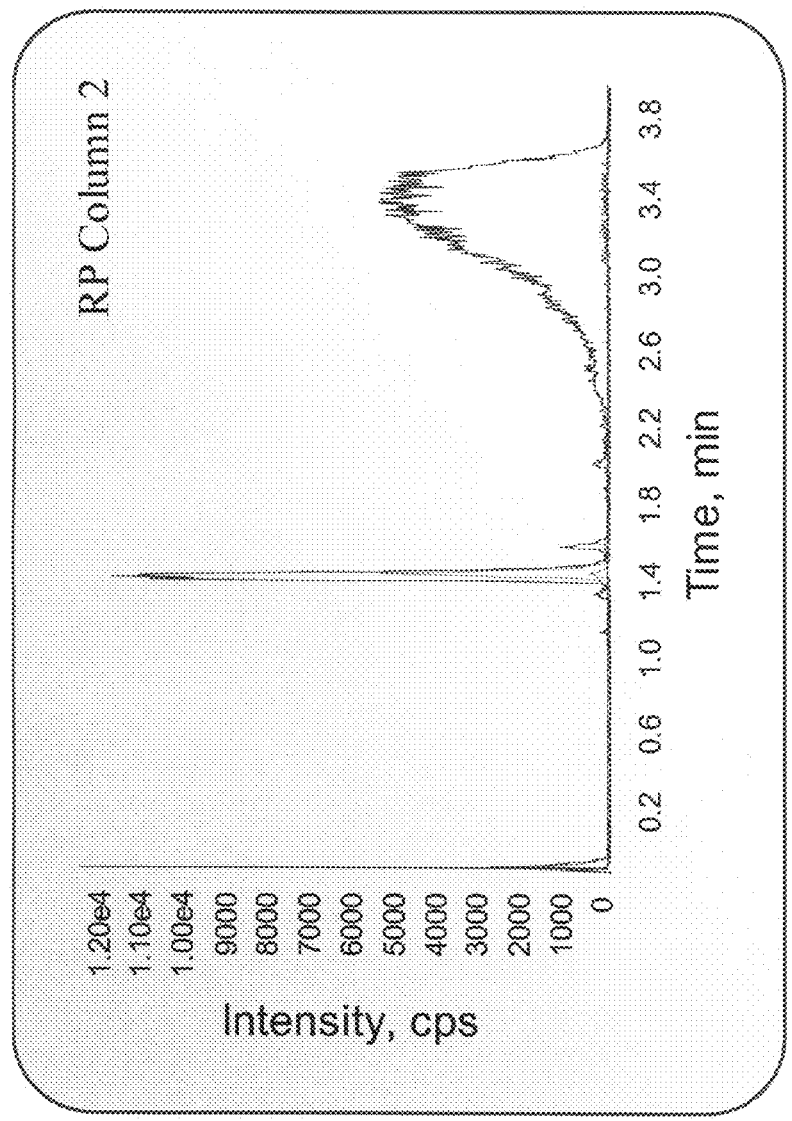
Figure 5F:
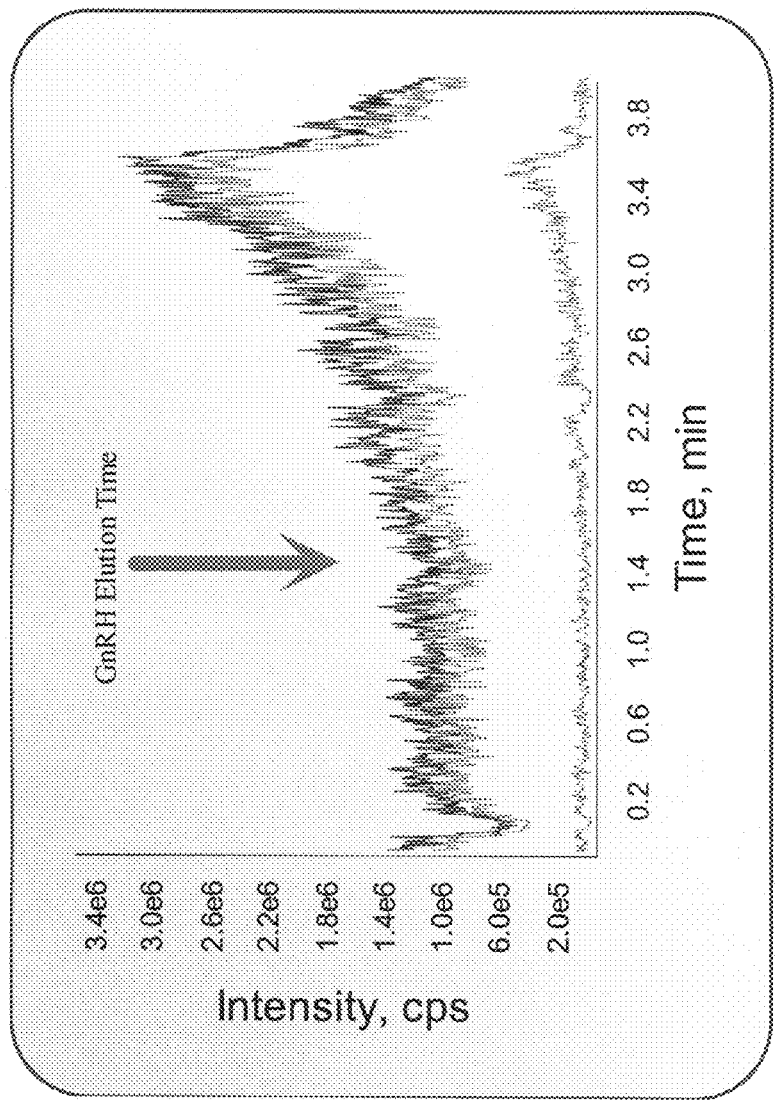
Figure 5G:
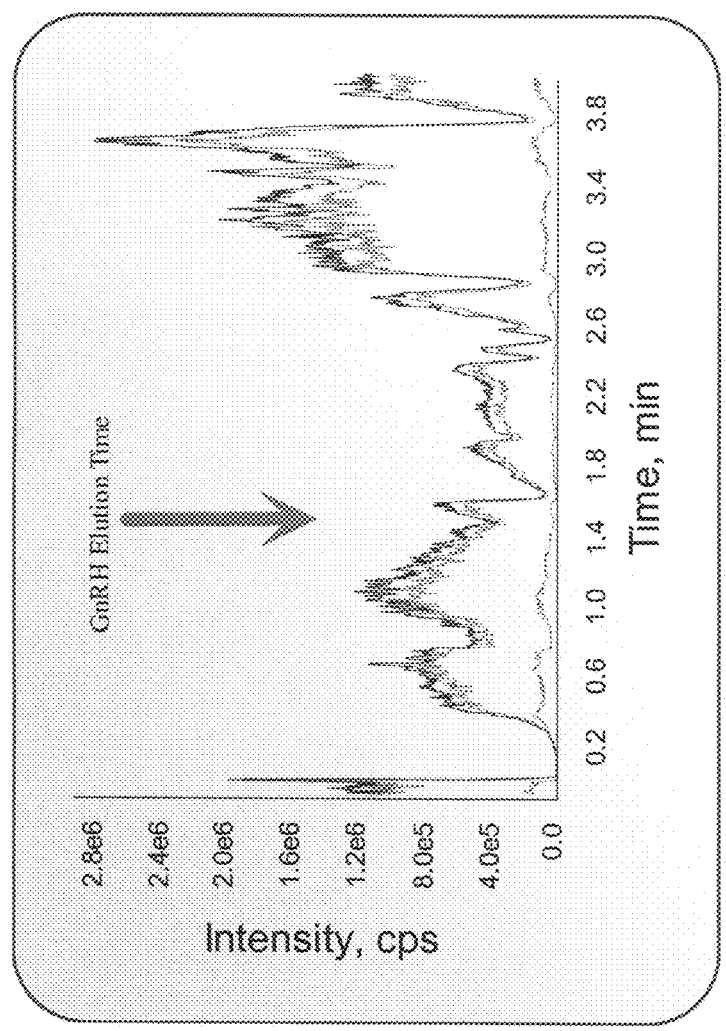
Figure 5H:
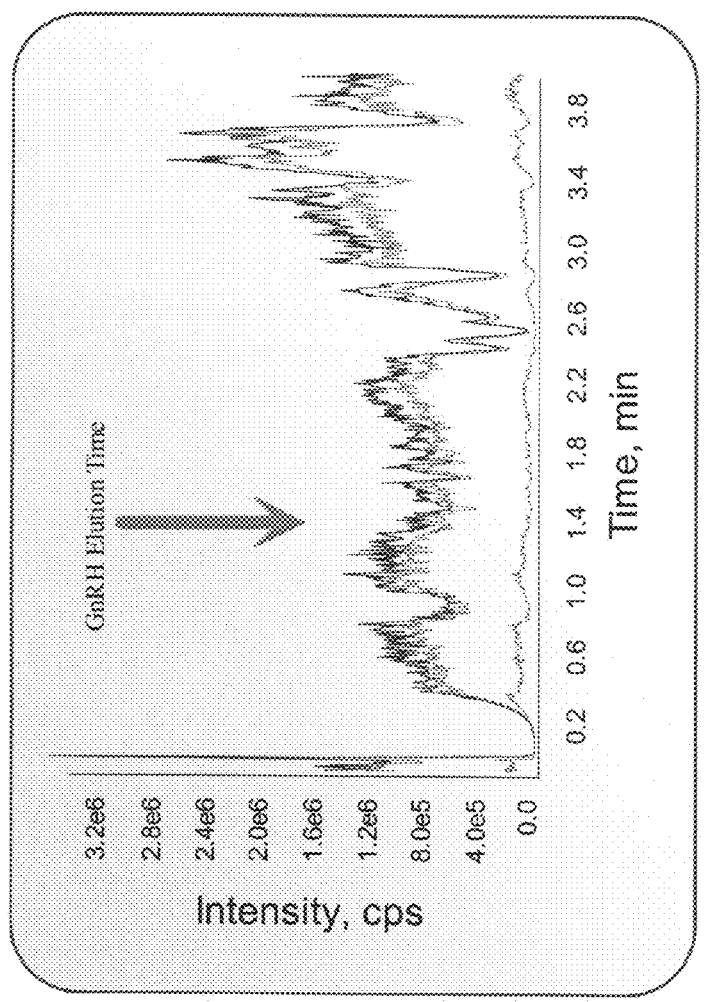

FIG. 5A shows the profile of neat GnRH injected into a Zorbax Stable Bond (SB) C-18 reverse phase column (RP Column 1) and provides the timeline for GnRH elution for this column. It can be seen that GnRH elutes at about 1.6 min with separation of contaminants at 0.4 and 1.3 minutes. Next, various solvents were evaluated for extraction and precipitation of the GnRH. The results of solvent extraction were compared to water (i.e., a negative control) (FIG. 5B). It was found that extraction and precipitation of GnRH with methanol resulted in the co-purification of compound(s) that could inhibit detection of GnRH (FIG. 5C). In contrast, extraction and precipitation of GnRH with acetonitrile resulted in a reduced amount of interfering compounds that can inhibit detection of GnRH at approximately 1.6 minutes (FIG. 5D). A similar series of studies was performed using other reverse phase extraction columns. Results are shown (FIG. 5E-5H) for a Thermo Biobasic C-18 column (50×2.1 mm, 5 µm) (RP Column 2). GnRH elution at approximately 1.4 minutes with slight resolution from interfering compounds (i.e., interferants) is shown (FIG. 5E). Again, it was found that as compared to neat GnRH (FIG. 5E) or water (FIG. 5F), extraction of samples with methanol resulted in the co-purification of compound(s) that could inhibit detection of GnRH (FIG. 5G), but that extraction with acetonitrile provided a good selectivity for GnRH purification (FIG. 5H).

Thus, in certain embodiments, a first dimension RPLC using either RP column 1 or RP column 2, eluted with an increasing gradient of acetonitrile:aqueous buffer (i.e., the amount of acetonitrile to aqueous is increasing during the elution of the column) provides acceptable selectivity for GnRH measurement. It can be seen, however, that the results with RP Column 1 (FIG. 5D) may provide a slightly cleaner signal than RP Column 2 (FIG. 5H). However, due to the relatively high amount of aqueous solvent in the GnRH fractions eluted from the RP column, these samples may not provide sufficient sensitivity for MS/MS detection. In an embodiment, the elution buffer for RPLC is as described in the examples herein.

Second Dimension Sensitivity Evaluation (Hydrophilic Interaction)

In certain embodiments, another type of chromatography may improve resolution and sensitivity of measurement of an analyte of interest such that the sample can be analyzed by mass spectrometry. As discussed herein, hydrophilic interaction liquid chromatography (HILIC) may be used for sample purification either alone, or in combination with RPLC. In certain embodiments, both the RP column 1 and the RP column 2 may be evaluated with a second dimension HILIC separation. Or, other RP columns may be used.

Figure 6B:
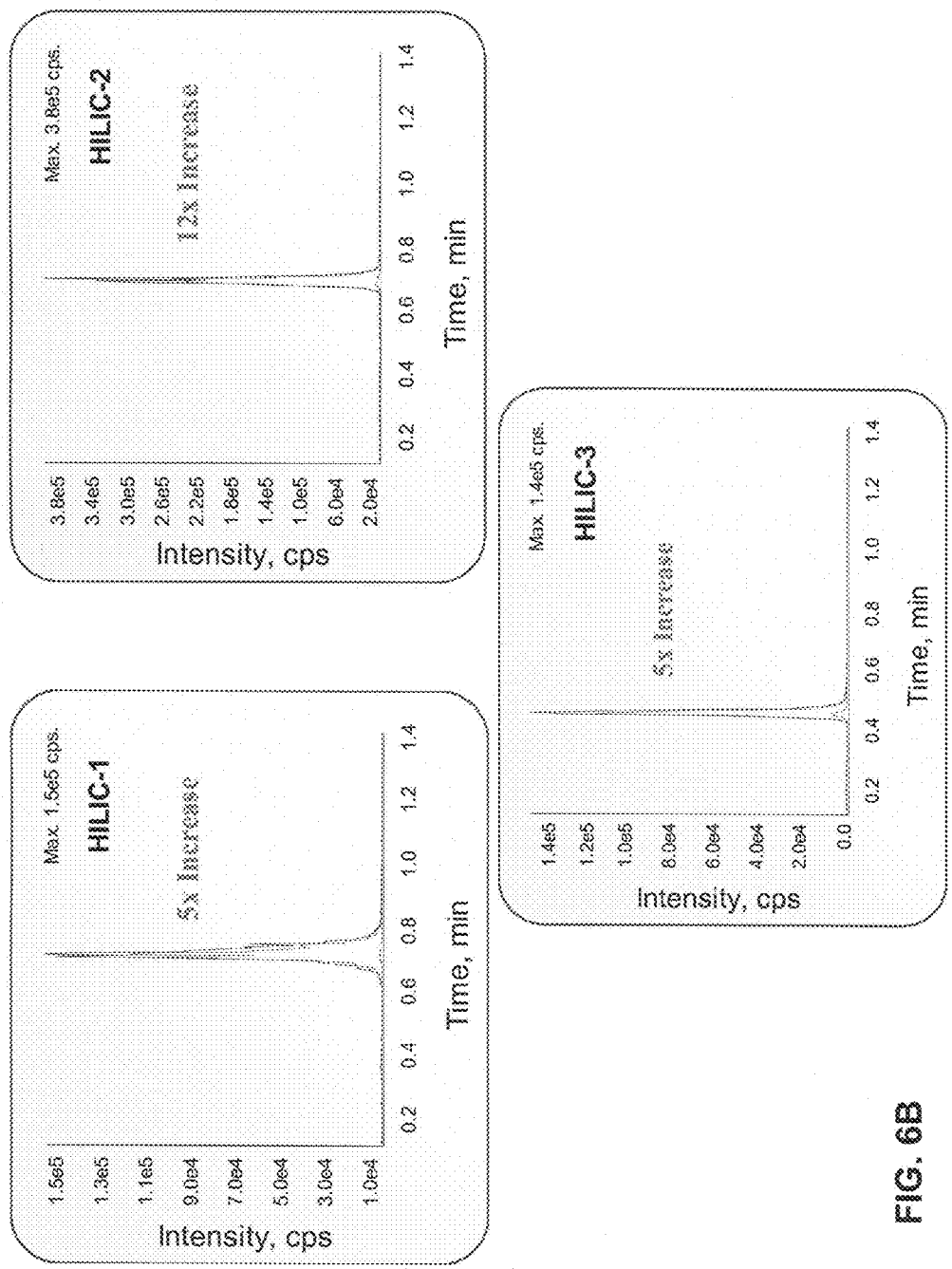

In some embodiments, detection of neat GnRH (10 ng/mL) shows a significant increase in sensitivity using HILIC columns (FIG. 6A) as opposed to reverse-phase columns (FIG. 6B). In an embodiment, this increase in sensitivity is because polar analytes, such as charged or hydrophilic peptides or proteins, elute in an organic rich stream that is more amenable to analysis by electrospray and/or nanospray MS than analytes in a polar solvent. A variety of HILIC columns may be used. Examples columns are as follows: Thermo Cyanopropyl silica (50×2.1 mm, 5 um) (HILIC column 1); Thermo Betasil silica (50×2.1 mm, 5 um) (HILIC column 2); and Thermo Hypersil silica (50×2.1 mm, 5 um) (HILIC column 3). In many cases, however, gains in sensitivity may be lost when precipitated plasma samples were injected directly onto RPLC (FIG. 7A) or HILIC columns (FIG. 7B) as a single dimension separation as compared to use of both columns (FIG. 7C). Again, in FIGS. 6A and 6B, and FIG. 7, the overlapping two plots are separate transitions for GnRH which may be used as an internal control to validate that the analyte (GnRH) is the compound being monitored. Also shown is the transition for the labeled internal standard: 603.1/249.1 and 603.1/178.0 (i.e., plots having about 1/10 intensity as the two plots for the GnRH analyte in FIG. 6).

In an embodiment, however, the combination of RP and HILIC chromatography provides the required specificity and sensitivity for GnRH assay. As shown in FIG. 7, comparison of the 100 pg/mL plasma standard (following protein precipitation with acetonitrile, evaporation, and reconstitution) shows greater than 10-fold enhancement in signal intensity attained through the use of Reverse-Phase/Normal-Phase LC-LC-MS/MS. By combining the optimal RP and HILIC columns from the above experiments, embodiments of the resulting 2D-LC-MS/MS method may achieve a desired LLOQ of 10 pg/mL and represents an analytical workflow that is useful for the analysis of most peptides and proteins from human samples.

Assay Performance

Embodiments of the methods of the present invention are suitable for the analysis of bioanalytes from clinical samples. Data showing the representative chromatograms, calibration curves, and inter-assay comparisons of the LC-MS/MS and 2D-LC-MS/MS methods of the present invention are provided in FIG. 8. Data showing the validation bias due to ionization effect and recovery for selected analytes are provided in FIG. 9. As known by those in the art, acceptable values based on the FDA and CLIA regulations are ≤20% bias or imprecision (% CV) at the LLOQ and ≤15% over the remainder of the assay. See e.g., FDA Guidance: 1.1 Guidance for Industry, Bioanalytical Method Validation, FDA, May 2001, BP, and CLIA Regulation: 42 CFR 493.1253 Standard: Establishment and verification of performance specifications. Subart K, Quality System for Non-waived Testing. Thus, as used herein, "acceptable" or "good" indicates that the assay or aspect of the method being measured meets the NCCLS, FDA and CLIA criteria.

As shown in FIG. 8, in certain embodiments, the assay exhibits a LLOQ of 10 pg/mL (FIG. 8A) and an ULOQ of about 1000 pg/mL (FIG. 8B) for GnRH. FIG. 8C shows a calibration curve as performed using an embodiment of the method of the present invention. To generate the calibration curve, spiked blank plasma standards were prepared at seven concentrations and used to generate a weighted (1/x) linear regression calibration curve. The calibration curve covered the range from 10-1000 pg/mL for GnRH. Calibration curves were analyzed in duplicate in each batch (FIG. 8C). It can be seen that the assay provides acceptable linearity. Also, carryover as assessed on a blank was found to be acceptable (FIG. 8D).

Figure 8A:
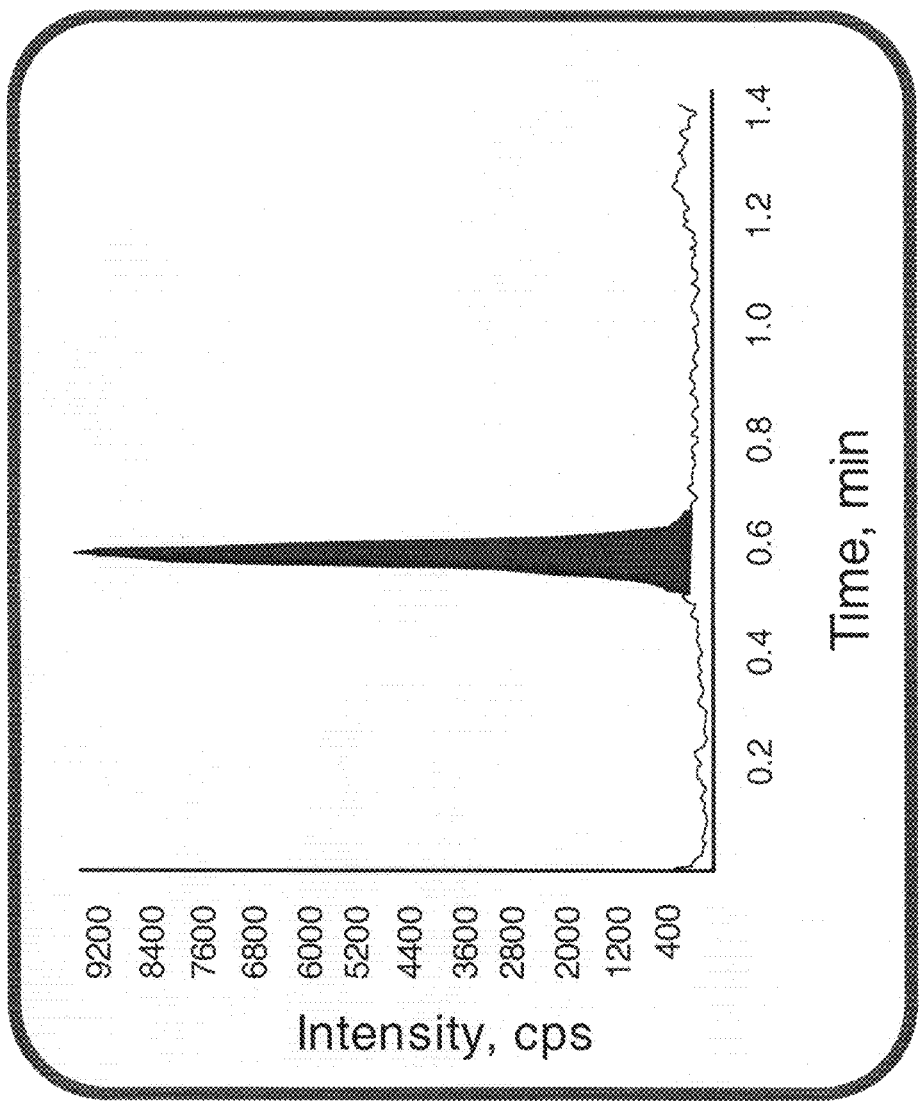
Figure 8B:
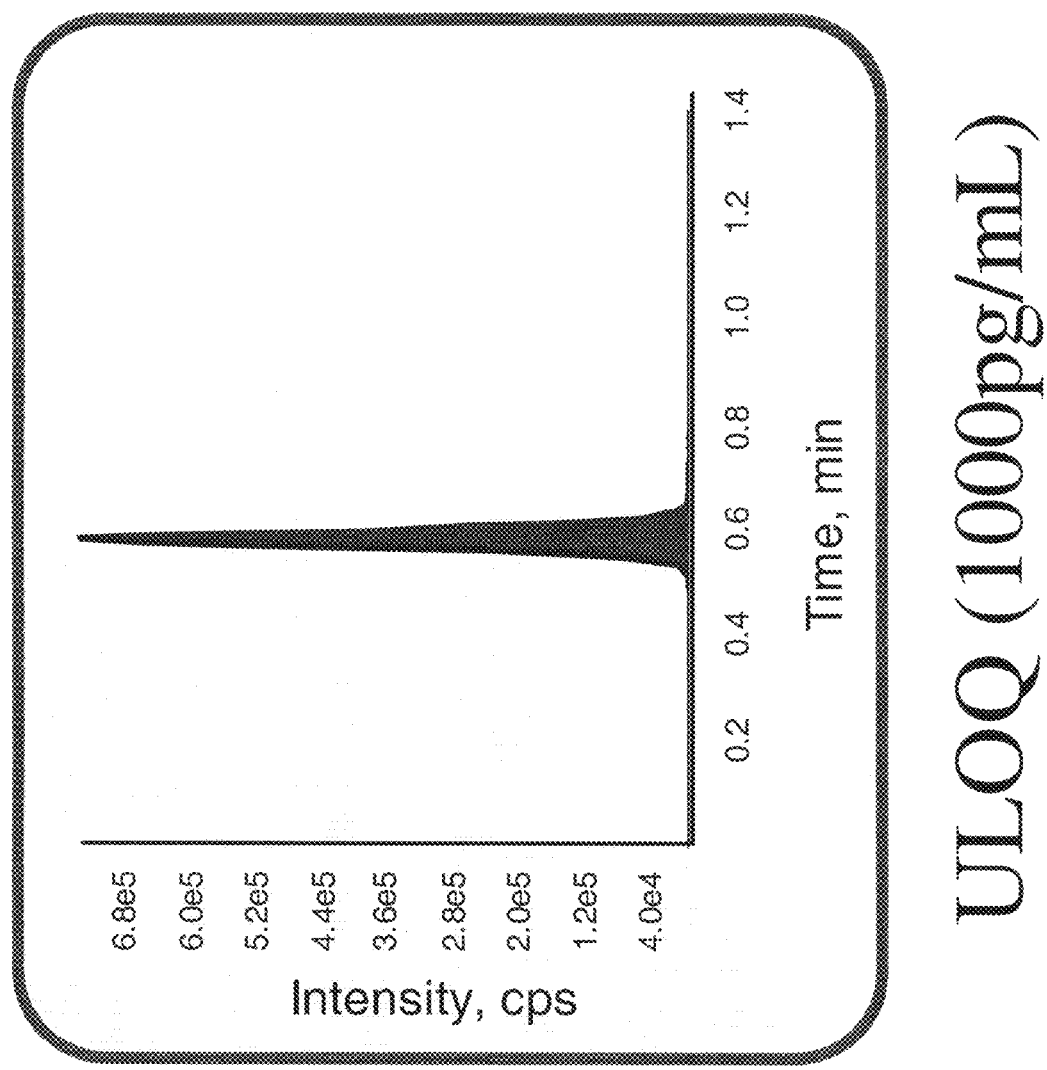
Figure 8C:
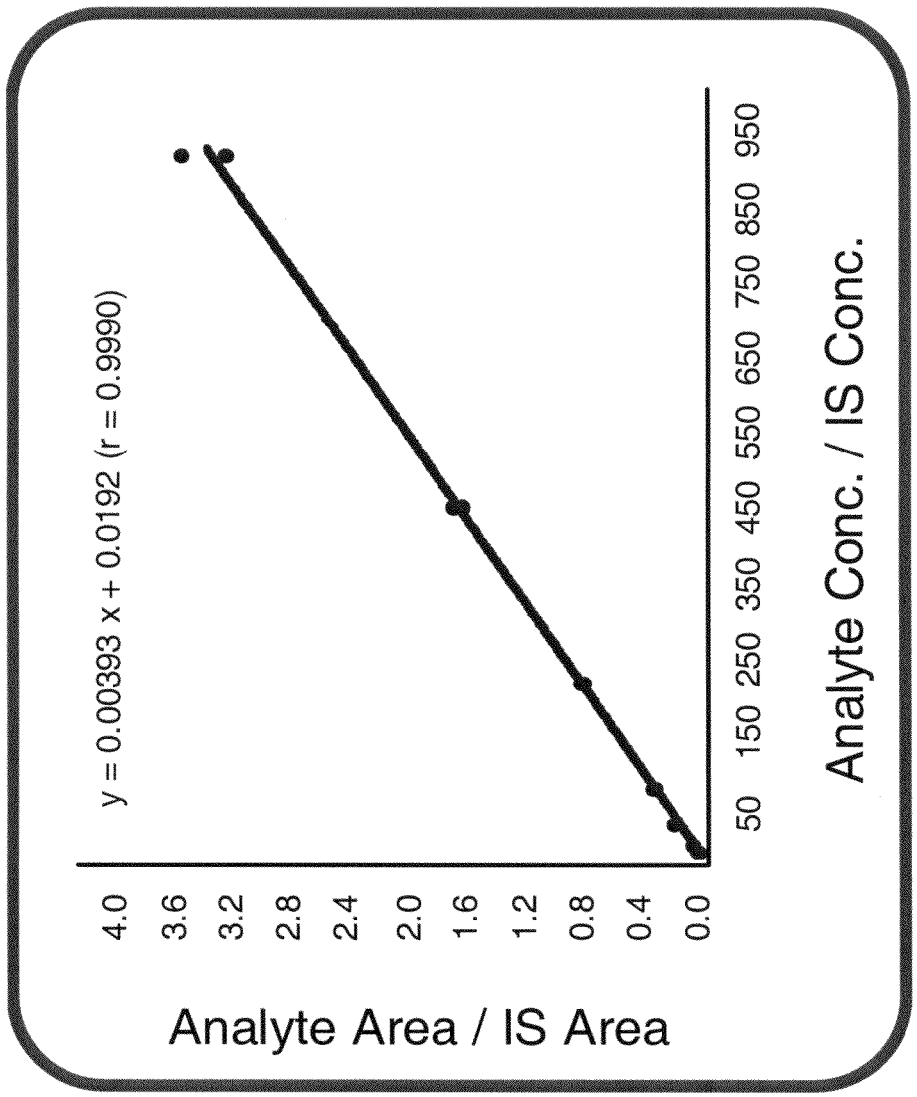
Figure 8D:
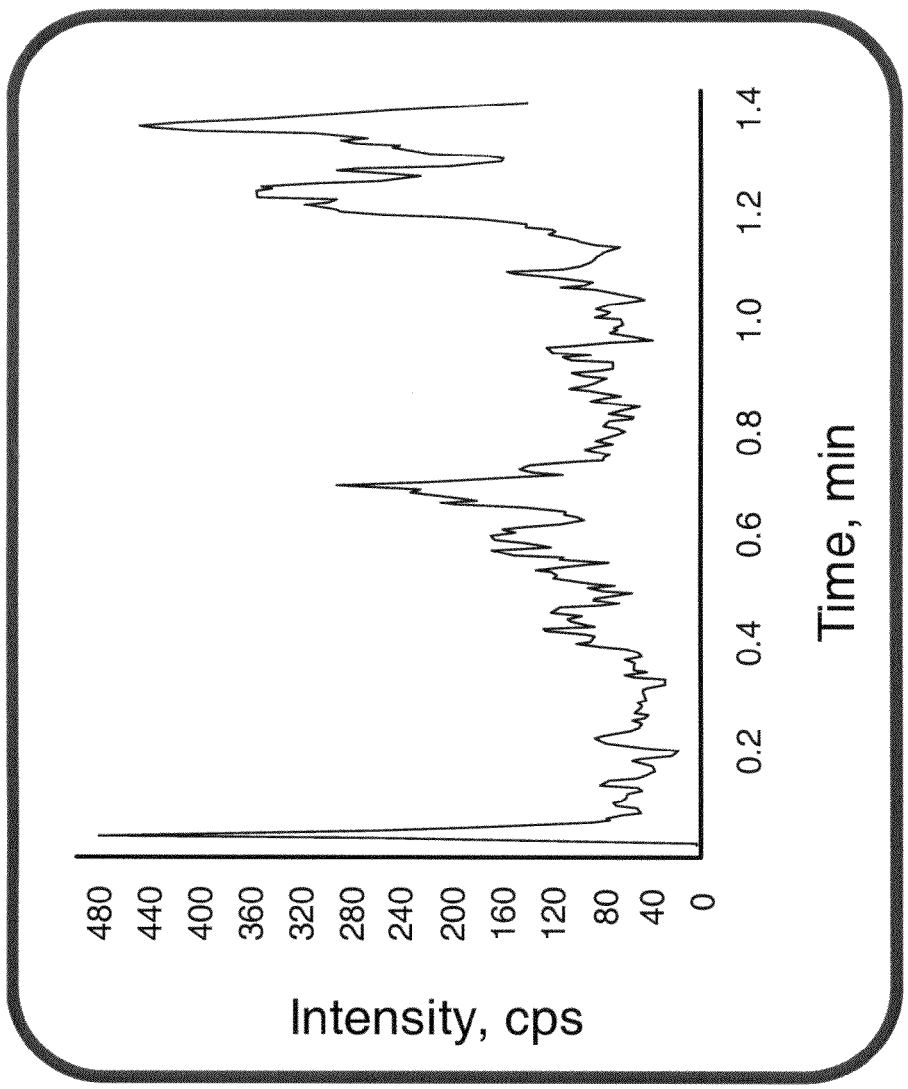
Figure 8E:
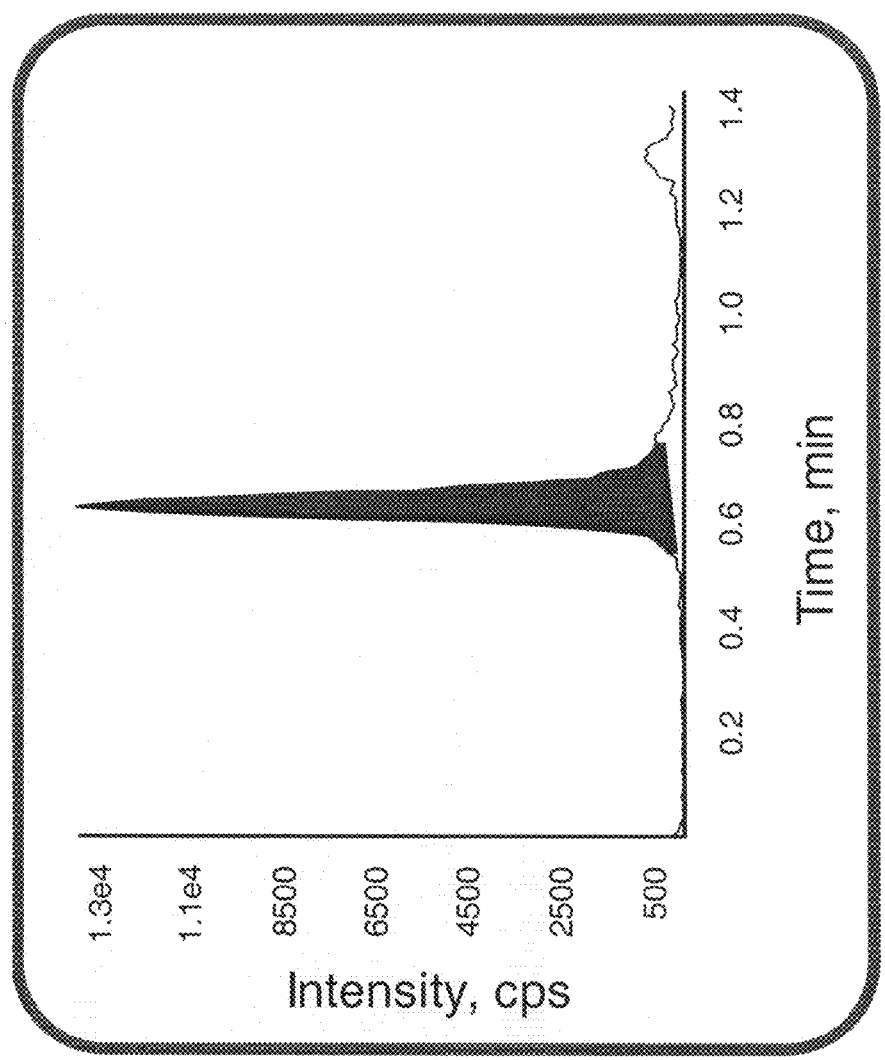
Figure 8F:
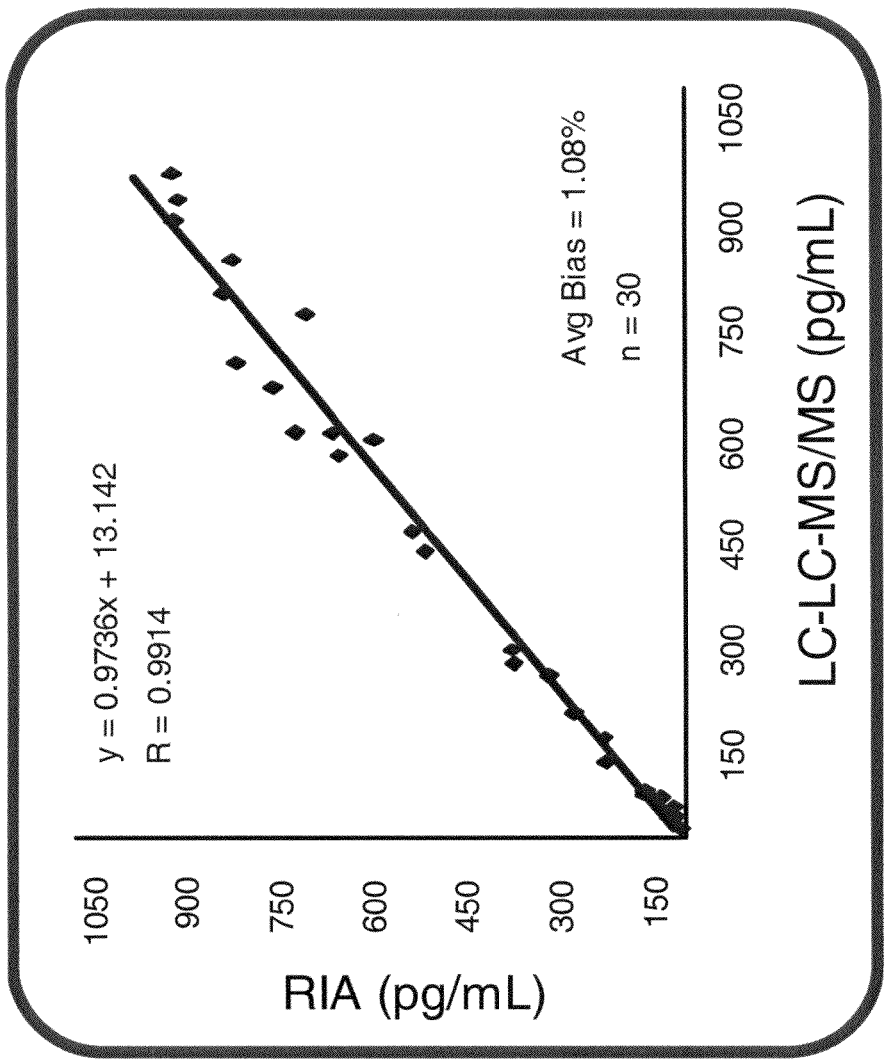

FIG. 8E provides the results for a patient assay as performed according to one embodiment of the present invention. Cross-validation of samples analyzed by Radioimmunoassay (RIA) against LC-LC-MS/MS indicated acceptable bias. Comparison using a scatter plot produced acceptable linearity (FIG. 8F).

A summary of the accuracy and precision of the assay of the present invention is shown in FIG. 9A. Recovery data (e.g., bias %) for lipemic samples, plasma samples and whole blood is shown in FIG. 9B. Accuracy and precision were validated using 3 separate validation batches. Quality control (QC) samples at 30, 100, 400 and 800 pg/mL were prepared in pooled plasma to determine precision. Calibrator samples at 10, 500 and 1000 pg/mL were prepared in blank plasma to determine accuracy. In certain embodiments, hemolyzed samples may fail to pass validation criteria and thus, may not be acceptable for use in the assay as such samples may exhibit >15% bias. As discussed in the Examples herein, spike and recovery experiments may be performed using a pooled plasma QC containing low levels of GnRH. Also, as shown in the examples herein, assay specificity may be shown for [(U-23C9, 15N)-Tyr5], [(U-23C6, 15N)-Leu7], [(U-19C5, 15N)-Pro9]-Gonadorelin (i.e., GnRH having the sequence of pGlu-His-Trp-Ser-Tyr-Gly-Leu-Arg-Pro-Gly-$NH_2$ isopically labeled as indicated) (SEQ ID NO: 2) internal standard (IS). In performing the assay, a stable-labeled IS may be added to all samples (except for Double Blanks).

(LC)LC-MS/MS and LC-MS/MS Methods to Measure Biomarker Peptides and/or Proteins

A schematic of a method of the invention is provided in FIG. 10. As shown in FIG. 10, in one embodiment, the method may include a step of providing a biological sample, for example, a serum sample believed to contain one or more analytes of interest (4). The analyte may comprise an analyte such as a peptide or protein. In one embodiment, the peptide is GnRH.

In some embodiments, an appropriate internal standard is added to the sample (6) (FIG. 10). For example, for analysis of GnRH, [(U-23C9, 15N)-Tyr5], [(U-23C6, 15N)-Leu7], [(U-19C5, 15N)-Pro9]-Gonadorelin internal standard (IS) may be used. In yet other embodiments, structural analogs of the analyte of interest may be used. For example, similar types of labeled internal standards may be developed for other peptides. Such structural analogs may comprise compounds wherein a first chemical group is replaced with a second chemical group. In general, the groups are of similar chemical reactivity, but different mass, as for example, the replacement of a methyl ($—CH_3$) group with an ethyl ($—CH_2CH_3$) group or replacement of one or more amino acids in the peptide and/or protein with another amino acid.

In some embodiments, the analyte of interest (e.g., a peptide analyte) is partially purified by liquid-liquid extraction of the sample (8). In an embodiment, the liquid-liquid extraction is used to concentrate and partially purify the analyte. For example, for analysis of a peptide, such as GnRH, the liquid extraction may be used to remove modified proteins and/or peptides, such as phosphorylated, sulfated and glucoronidated peptides. Also, the liquid extraction may remove lipids and/or fibrinogen from the samples. For example, in one embodiment, acetonitrile may be used for extraction of a peptide biomarker analyte. Or, other solvents may be used. As is known in the art, the solvents employed may be optimized to separate the analyte of interest from the sample. For example, the solvents used to extract GnRH from serum may not be the same solvent or solvent mix as used to extract GnRH from urine. Or, the solvents used to extract GnRH from serum may not be the same solvent or solvent mix as used to extract other peptides from serum.

Certain biomolecules may have a propensity to nonspecifically bind to proteins or other biomolecules. For example, certain peptides, e.g., GnRH, and/or hormones (e.g., testosterone, progesterone, cortisol) can non-specifically bind to proteins such as serum albumin, sex hormone binding globulin, and the like. For determination of the non-bound peptide, the sample may be treated to separate the free peptide from protein-bound peptides that is bound to proteins in the biological sample (e.g., serum).

For example, in one embodiment (not shown in FIG. 10), the sample may initially be dialyzed to separate the free peptide from a mixture of free and protein-bound peptide. In certain embodiments, multiple samples may be processed concurrently. For example, the dialysis may be performed using a multiwell dialysis plate which allows for the dialysis of multiple samples at one time. In certain embodiments 96 well plates are used. In this way, multiple samples are processed to comprise a high throughput assay.

The dialysis buffer may, in certain embodiments, be isotonic and contain gelatin. The gelatin may be used over a range of concentrations depending upon the nature of the membranes and hardware used for dialysis. In alternate embodiments, the gelatin may be in a range of from about 0.1 to 10 mg/mL. In an embodiment, the gelatin is at about 1 mg/mL. In certain embodiments, the buffer used for dialysis comprises multiple endogenous salts to provide a buffer that is isotonic with the serum sample to thereby negate any potential dilution effects and/or disruptions to the ratio of bound peptide to free peptide in the sample. Also, gelatin may be included to prevent adsorptive losses of free peptide onto the dialysis membrane or the sample chamber. Gelatin may act as a carrier on the dialysate side of the 96-well plate to ensure free peptide remains in the dialysate solution. Generally, gelatin does not bind free peptide and thus, does not affect the ratio of bound peptide to free peptide in the sample on the sample side of the membrane.

For the analysis of free peptides, an extraction (e.g., liquid-liquid extraction, or solid-phase extraction or immunoaffinity) step may be performed after the dialysis. The liquid extraction may be designed to remove residual salts and/or other additives which are used in the dialysis solution and/or remain from the sample, but that may interfere with the MS analysis. Thus, in one embodiment, the dialysate comprising free peptide is extracted with a solvent such as ethyl acetate:hexane:methanol. In another embodiment, the dialysate or undialyzed sample may be diluted with a solution of methanol or acetonitrile containing a stable labeled internal standard and directly injected onto the LC-MS/MS system for analysis.

Where the dialyzed sample is extracted, the internal standard addition may include a protein to prevent the free peptide from sticking to the walls of the sample container. Addition of protein (e.g., bovine serum albumin) can minimize losses in extraction and recovery for liquid-liquid extraction. Where extraction is not performed, the internal standard may be added in methanol or a similar solvent used for LC.

In yet other embodiments, the peptide may be partially purified by binding to an antibody that specifically recognizes the peptide. The antibody may be bound to a solid phase, such as a bead or other type of carrier.

As is known in the art, in some embodiments, where extraction is used, the organic extract may be transferred to a fresh tube and then back-washed. For example, in an embodiment, the solvent may be back-washed with aqueous sodium hydroxide (pH of about 12) to further purify the sample. The back-wash may, in certain embodiments, remove additional lipids or interfering analytes from the sample.

The extract supernatant may then be evaporated and the sample reconstituted (9). For example, for analysis of GnRH, the sample may be reconstituted in 70:30 water:methanol.

Or, in certain embodiments, the sample is not partially purified, but may be diluted into the solvent used for LC and/or MS.

Still referring to FIG. 10, the method may further include liquid chromatography as a means to separate the analyte of interest from other components in the sample. In an embodiment, two liquid chromatography steps are used. For example, the method may comprise a first reverse phase extraction column liquid chromatography (10), and transfer of the analyte of interest to a second analytical column (12). In one embodiment, the analytical column is a hydrophilic interaction LC (HILIC) analytical column (12), Or, in some cases only the analytical chromatography, e.g., HILIC, may be required.

The first extraction liquid chromatography column may, in certain embodiments, comprise a step whereby the analytes of interest are separated from a majority of contaminants. Thus, in certain embodiments, the first column provides the majority of selectivity for the procedure. For example, the sample may be applied to a Zorbax Stable Bond (SB) C-18 reverse phase column (RP Column 1) or a Thermo Biobasic C-18 column and eluted with an increasing gradient of acetonitrile.

The second analytical liquid chromatography column may, in certain embodiments, comprise a step whereby the analytes of interest are concentrated, to thereby increase sensitivity for analysis by mass spectrometry (MS) by delivering analytes to the interface in a solvent chemistry that enhances ionization efficiency and thus, detection sensitivity. Depending upon the analyte of interest, a variety of analytical columns known in the art may be used as needed to provide good purification. In certain embodiments, the HILIC analytical column may comprise particles having a diameter less than or equal to about 5 μm. In some embodiments, the analytical column is a functionalized silica or polymer-silica hybrid, or a polymeric particle or monolithic silica stationary phase, such as a Thermo Cyanopropyl silica (e.g., 50 mm×2.1 mm; 5 um) column, a Thermo Betasil silica (e.g., 50 mm×2.1 mm; 5 um) column, or a Thermo Hypersil silica (e.g., 50 mm×2.1 mm; 5 um) column.

If two liquid chromatography steps are employed, the eluted analytes may be transferred to the analytical column in a manner such that the sample is concentrated upon application to the analytical column. In some embodiments, the eluted analytes are transferred to the analytical column via a heart-cutting technique. In some embodiments, a chromatofocusing procedure is used to transfer and focus the analytes on the analytical column. Also in some embodiments, a column-switching procedure is used to transfer the analytes to the analytical column. The analytes may then be separated on the analytical column (16) and the fraction containing the analyte of interest is eluted. In an embodiment, the second column in run in a manner to maximize throughput, and to provide the sample in a reduced volume of solvent.

The separated analytes may then be introduced into a mass spectrometer (MS) system (20). In some embodiments, a tandem MS/MS system is used. As is known by those of skill in the art, in tandem MS spectrometry, the precursor ion is selected following ionization, and that precursor ion is subjected to fragmentation to generate product (i.e., fragment) ions, whereby one or more product ions are selected for detection. Each precursor ion is known as a transition, and monitoring of one or more transitions is known as selected reaction monitory (SRM) or multiple reaction monitoring (MMR). Thus, in certain embodiments, the MS/MS analysis comprises at least one of SRM or MMR.

The analyte of interest may then be quantified based upon the amount of the characteristic transitions measured by tandem MS. In some embodiments, the tandem mass spectrometer comprises a triple quadrupole mass spectrometer. In some embodiments, the tandem mass spectrometer is operated in an electrospray ion (ESI) mode. In some embodiments, the electrospray is operated in a positive ion mode. In some embodiments, a nanospray emitter is used. In some embodiments, the quantification of the analytes and internal standards is performed in the selected reaction monitoring mode (SRM). Or, other methods of ionization such as the use of inductively coupled plasma, or MALDI, or SELDI, APCI, or APPI may be used for ionization.

In some embodiments, the back-calculated amount of each analyte in each sample may determined by comparison of unknown sample response or response ratio when employing internal standardization (such as the addition of radiolabelled Gonadorelin as described herein) to calibration curves generated by spiking a known amount of purified analyte material into a standard test sample, e.g., charcoal stripped human serum. In one embodiment, calibrators are prepared at known concentrations and analyzed as per the analyte methodology to generate a response or response ratio when employing internal standardization versus concentration calibration curve.

Systems for Quantification of Endogenous Biomarkers

FIG. 11 shows an example system of the present invention. It will be understood that the system as shown in FIG. 11 is illustrative in nature, such that some of the stations may actually be combined in practice whereas other stations depicted as single stations may in fact be multiple stations.

Figure 11A:
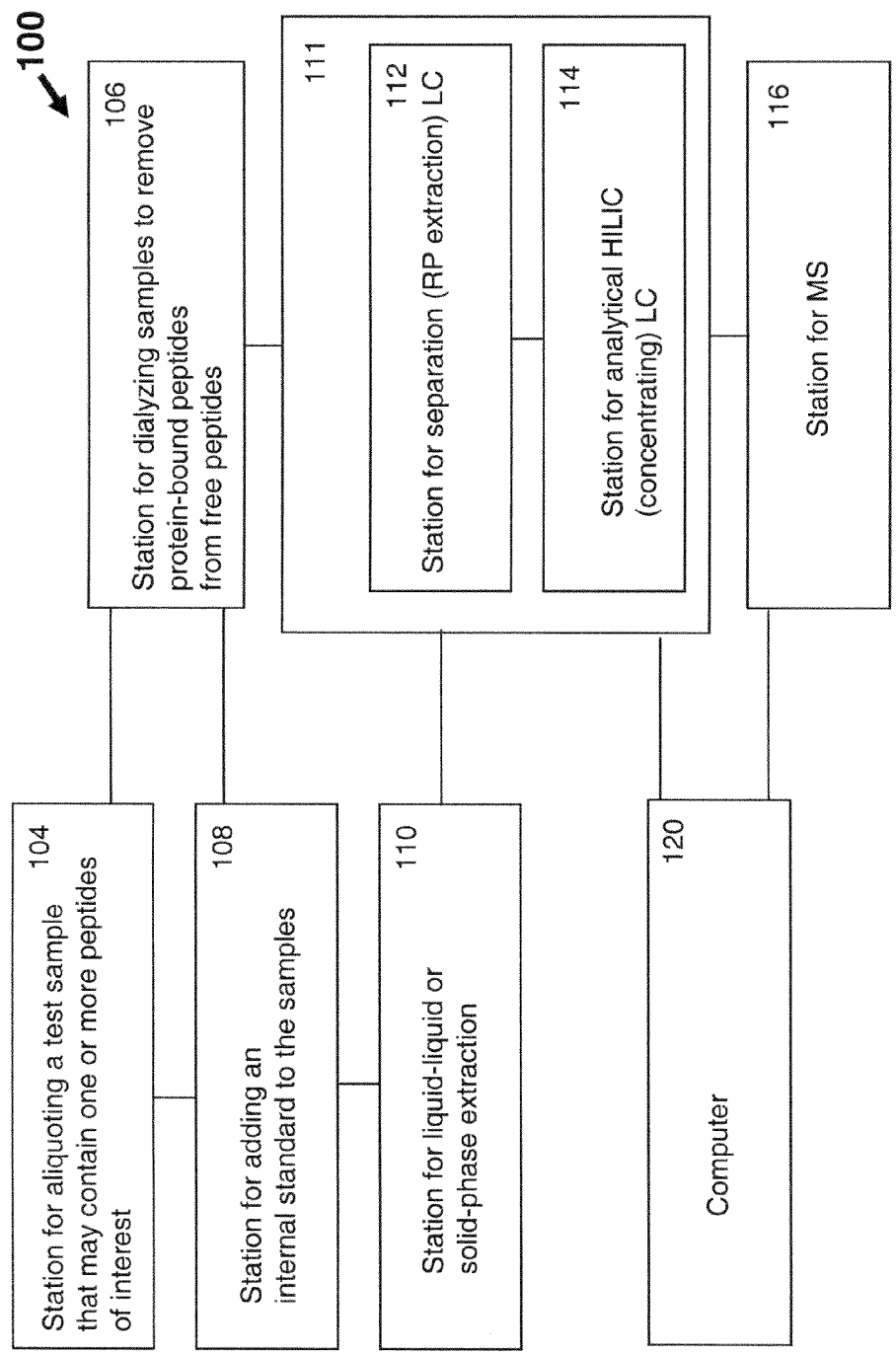

Thus, FIG. 11A shows one embodiment of a system of the present invention. As shown in FIG. 11A, the system may comprise a station for aliquoting a sample (104) that may comprise an analyte of interest into sampling containers. In one embodiment, the sample is aliquoted into a container or containers to facilitate liquid-liquid extraction, or solid-phase extraction, dialysis, immunoaffinity purification, or sample dilution. The station for aliquoting may comprise receptacles to discard the portion of the biological sample that is not used in the analysis.

In one embodiment, the system may comprise a station for dialysis (106) of the sample or a portion thereof. The container for dialysis may comprise a multi-well plate. The station for dialysis may comprise a rotator oven, multi-chamber pipettes for sample transfer, as well as receptacles to discard the portion of the biological sample that is not used in the analysis.

The system may comprise a station for adding an internal standard to the sample (108). In an embodiment, the internal standard comprises the analyte of interest labeled with a non-natural isotope. Thus, the station for adding an internal standard may comprise safety features to facilitate adding an isotopically labeled internal standard solutions to the sample.

The system may also, in some embodiments, comprise a station (110) for at least one of liquid-liquid extraction or solid-phase extraction. The station for liquid-liquid extraction may comprise equipment and reagents for addition of solvents to the sample and removal of waste fractions. In some cases, an isotopically-labeled internal standard is used to standardize losses of the analyte that may occur during the procedures. Thus, the station for liquid-liquid extraction (or sample dilution, solid-phase extraction, or immunoaffinity purification) may comprise a hood or other safety features required for working with solvents.

Additionally or alternatively, the system may comprise as station for solid-phase extraction. Generally, solid phase extraction is an extraction method that uses a solid phase and a liquid phase to isolate one, or one type, of analyte from a solution. Thus, the station for solid-phase extraction may comprise a column or other type of container that is filled with the solid phase, a dispenser to apply the sample to the solid phase, and a solvent that is used to elute the analyte from the solid phase.

In other embodiments, the sample may comprise a station for immunoaffinity purification. The station for immunoaffinity purification may comprise a matrix to which an antibody to the analyte of interest is bound. Also, the station for immunoaffinity purification may comprise reagents for washing the matrix, applying the analyte and eluting the analyte. In one embodiment, the immunoaffinity purification station comprises an antibody to GnRH.

The system may also comprise a station for liquid chromatography (LC) of the sample 111. As described herein, in an embodiment, the station for liquid chromatography may comprise a reverse phase extraction liquid chromatography column (112). The station for liquid chromatography may comprise a column comprising the stationary phase, as well as containers or receptacles comprising solvents that are used as the mobile phase. In an embodiment, the mobile phase comprises a gradient of acetonitrile and buffered water, or other miscible solvents with aqueous volatile buffer solutions. Thus, in one embodiment, the station may comprise the appropriate lines and valves to adjust the amounts of individual solvents being applied to the column or columns. Also, the station may comprise a means to remove and discard those fractions from the LC that do not comprise the analyte of interest. In an embodiment, the fractions that do not contain the analyte of interest are continuously removed from the column and sent to a waste receptacle for decontamination and to be discarded. A variety of reverse phase extraction LC systems may be used as described herein.

The system may also comprise an analytical LC column (114) either alone or in a multidimensional mode with a RP extraction column. In certain embodiments, the analytical column is of a polar nature facilitating HILIC separation (e.g., a silica, cyano or amine column). The analytical column may facilitate further purification and concentration of the analyte of interest as may be required for further characterization and quantification.

As discussed in more detail below, both the extraction column(s) and/or the analytical column(s) may be operated manually, or may be "on-line". In an embodiment, the on-line columns are computer controlled.

Also, the system may comprise a station for characterization and quantification of the analyte of interest. In one embodiment, the system may comprise a station for mass spectrometry (MS) of the analyte. In an embodiment, the station for mass spectrometry comprises a station for tandem mass spectrometry (MS/MS). Also, the station for characterization and quantification may comprise a computer and software for analysis of the MS/MS results. In an embodiment, the analysis comprises both identification and quantification of the analyte of interest.

In some embodiments, one or more of the purification or separation steps can be performed "on-line." As used herein, the term "on-line" refers to purification or separation steps that are performed in such a way that the test sample is disposed, e.g., injected, into a system in which the various components of the system are operationally connected and, in some embodiments, in fluid communication with one another. The on-line system may comprise an autosampler for removing aliquots of the sample from one container and transferring such aliquots into another container. For example, an autosampler may be used to transfer the sample after extraction onto an RPLC extraction column. Additionally or alternatively, the on-line system may comprise one or more switching valves for injecting the fractions isolated from the extraction columns onto the HILIC analytical column. Additionally or alternatively, the on-line system may comprise one or more injection ports for injecting the LC purified sample into the MS system. Thus, the on-line system may comprise one or more columns, including but not limited to, an extraction column, including a RPLC extraction column, and in some embodiments, an HILIC analytical column. Additionally or alternatively, the system may comprise a detection system, e.g., a mass spectrometer system. The on-line system may also comprise one or more pumps; one or more valves; and necessary plumbing. In such "on-line" systems, the test sample and/or analytes of interest can be passed from one component of the system to another without exiting the system, e.g., without having to be collected and then disposed into another component of the system.

In some embodiments, the on-line purification or separation method can be automated. In such embodiments, the steps can be performed without the need for operator intervention once the process is set-up and initiated. For example, in one embodiment, the system, or portions of the system may be controlled by a computer or computers (120). Thus, in certain embodiments, the present invention may comprise software for controlling the various components of the system, including components used for chromatographic separation, e.g., pumps, valves, autosamplers, as well as components used for mass spectrometry. Such software can be used to optimize the extraction process through the precise timing of sample and solute additions and flow rate.

Although some or all of the steps in the method and the stations comprising the system may be on-line, in certain embodiments, some or all of the steps may be performed "off-line." In contrast to the term "on-line", the term "off-line" refers to a purification, separation, or extraction procedure that is performed separately from previous and/or subsequent purification or separation steps and/or analysis steps. In such off-line procedures, the analyte of interest typically is separated, for example, on an extraction column, by liquid/liquid extraction, by solid-phase extraction, or by immunoaffinity purification from the other components in the sample matrix and then collected for subsequent introduction into another chromatographic or detector system. Off-line procedures typically require manual intervention on the part of the operator.

The methods and systems of the present invention may use mass spectrometry to detect and quantify the analyte of interest. The terms "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes and the amplitude of the RF signal. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, the selectivity of the MS technique can be enhanced by using "tandem mass spectrometry," or "MS/MS." See, e.g., U.S. Pat. No. 6,107,623, entitled "Methods and Apparatus for Tandem Mass Spectrometry," which is hereby incorporated by reference in its entirety. Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter to select those ions having a particular mass-to-charge ratio. These ions are then fragmented, typically by collisions with neutral gas molecules in a suitable ion containment device, to yield product (fragment) ions, the mass spectrum of which is recorded by a electon multiplier detector. The product ion spectra so produced are indicative of the structure of the precursor ion, and the two stages of mass filtering can eliminate ions from interfering species present in the conventional mass spectrum of a complex mixture.

In an embodiment, the methods and systems of the present invention use a triple quadrupole MS/MS (see e.g., Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means. In one embodiment, the instrument may comprise a quadrupole mass filter operated in the RF only mode as an ion containment or transmission device. In an embodiment, the quadropole may further comprise a collision gas at a pressure of between 1 and 10 millitorr. Many other types of "hybrid" tandem mass spectrometers are also known, and can be used in the methods and systems of the present invention including various combinations of magnetic sector analyzers and quadrupole filters. These hybrid instruments often comprise high resolution magnetic sector analyzers (i.e., analyzers comprising both magnetic and electrostatic sectors arranged in a double-focusing combination) as either or both of the mass filters. Use of high resolution mass filters may be highly effective in reducing chemical noise to very low levels.

For the methods and systems of the present invention, ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, atmospheric pressure ionization, nanospray, and inductively coupled plasma.

In those embodiments, such as MS/MS, where precursor ions are isolated for further fragmentation, collision-induced dissociation ("CID") may be used to generate the fragment ions for further detection. In CID, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, to attain the required analytical selectivity and sensitivity, the presently disclosed 2D-LC-MS/MS methods include multiplexed sample preparation procedures. For example, in certain embodiments dialysis of the sample is performed using a 96 well plates or multiple sample tubes (FIG. 11B). Additionally or alternatively, the multiplex system may comprise staggered multiplexed LC and MS sample inlet systems. Also, the methods and systems of the present invention may comprise multiple column switching protocols, and/or heart-cutting (LC-LC or 2D-LC) techniques, and/or LC separations prior to MS detection. In some embodiments, the methods and systems of the present invention may include a multiplexed two-dimensional liquid chromatographic system coupled with a tandem mass spectrometer (MS/MS) system, for example a triple quadrupole MS/MS system. Such embodiments provide for staggered, parallel sample input into the MS system.

Thus, as shown in FIG. 11B, four samples (132 A-D) may each be applied to individual RPLC extraction columns (134 A-D). Once the samples have each run through the extraction column, they may each be transferred directly (e.g., by column switching) to a second set of HILIC analytical columns (136 A-D). As each sample elutes from the analytical column, it may be transferred to the mass spectrometer (140) for identification and quantification (142).

A plurality of analytes can be analyzed simultaneously or sequentially by the presently disclosed LC-MS/MS and 2D-LC-MS/MS methods. Exemplary analytes amenable to analysis by the presently disclosed methods include, but are not limited to, polar small molecules (<100 daltons) proteins and/or peptides such as GnRH. One of ordinary skill in the art would recognize after a review of the presently disclosed subject matter that other similar analytes could be analyzed by the methods and systems disclosed herein. For example, optimization of key parameters for each analyte can be performed using a modular method development strategy to provide highly tuned bioanalytical assays. Thus, certain steps may be varied depending upon the analyte being measured as disclosed herein.

Also, embodiments of the methods and systems of the present invention may provide greater sensitivity than the sensitivities previously attainable for many of the analytes being measured. For example, through using this optimization procedure, an LOQ of about 10 picogram per milliliter (pg/mL), or less than 15 pg/mL, or less that 20 pg/mL, or less than 25 pg/mL is attained for the analysis of GnRH without the cumbersome derivatization processes historically required for LC-MS/MS analyses of steroids. Importantly, the low levels of detection allow for the analysis of small sample volumes, for example 100 μL, 200 μL, 500 μL, or less than 1 mL, which can be necessary to analyze pediatric sample volumes. Thus, the presently disclosed (LC)-LC-MS/MS methods can be used to measure levels of endogenous peptides such as GnRH in serum or plasma samples from children, women, and men.

Embodiments of the present invention may provide certain advantages. In certain embodiments, the methods and systems of the present invention may provide greater sensitivity than the sensitivities previously attainable for many of the analytes being measured.

Also, embodiments of the methods and systems of the present invention may provide for rapid throughput that has previously not been attainable for many of the analytes being measured. For example, using the methods and systems of the present invention, multiple samples may be analysed for endogenous proteins and/or peptides using 96 well plates and a multiplex system of four LC-MS/MS systems, significantly increasing the throughput.

As another advantage, the specificity and sensitivity provided by the methods and systems of the present invention may allow for the analysis of analytes from a variety of biological materials. For example, the LC-MS/MS and 2D-LC-MS/MS methods of the present invention can be applied to the quantification of analytes of interest in complex sample biological matrices, including, but not limited to, blood, serum, plasma, urine, saliva, and the like. Thus, the methods and systems of the present invention are suitable for clinical applications and/or clinical trials.

As additional potential advantages, in certain embodiments, the systems and methods of the present invention provide approaches for addressing isobaric interferences, varied sample content, including hemolysed and lipemic samples, while attaining low pg/mL limits of quantification (LOQ) of the target analytes. Accordingly, embodiments of the methods and systems of the present invention may provide for the quantitative, sensitive, and specific detection of clinical analytes used in the clinical diagnosis of disorders.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

EXAMPLES

A quantitative bioanalytical method for the determination of GnRH in human plasma using protein precipitation and LC-LC-MS/MS detection was developed and validated. In these examples, Gonadotropin Releasing Hormone (GnRH) was measured by mass spectrometric detection after protein precipitation. The analysis was performed using two-dimensional liquid chromatography separation with tandem mass spectrometric detection (LC-LC-MS/MS). Stable labeled isotopic GnRH was added as an internal standard (IS) to plasma aliquots.

In summary, samples were extracted with acetonitrile, evaporated, and reconstituted with Methanol:Water (30:70). An MDS-SCIEX API5000 triple quadrupole mass spectrometer, operating in positive ion electrospray (ESI) mode was used for detection. Quantification of analyte and internal standard was performed in selected reaction monitoring mode (SRM). The back-calculated amount of GnRH in each sample was determined from duplicate calibration curves generated by spiking known amounts of purified GnRH into human plasma from 10 to 1000 pg/mL. The results indicated that the assay should be able to measure pharmacologic levels for clinical trials following administration of synthetic GnRH in human plasma.

Example 1

Assay Validation a. Selectivity

The assay was shown to be specific for the analysis of GnRH. First, quadruplicate injections of blank plasma were used to determine the degree of blank matrix interference for six separate samples of plasma in the GnRH assay. An average interference at a level ≤±20% of LLOQ response was observed in 5 out of 6 lots of blank human plasma.

The matrix effect was also calculated at low, mid, and high level concentrations for GnRH and a single concentration for GnRH internal standard. A minimum of 4 samples per QC level were analyzed to determine the matrix effect for both the analyte (GnRH) and the IS. It was found that the resulting matrix effect was ≤±15% at both the analyte and IS retention times. As used herein, the matrix effect=[(Mean Analyte to Internal standard ratio in pooled plasma)/Mean Analyte to Internal standard ratio in water)]-1, expressed as a percentage.

Next, the effect of heparin as an anticoagulant was tested. A first aliquot of blood from one healthy volunteer was drawn into a vacutainer containing sodium heparin, and a second aliquot was drawn into a vacutainer containing potassium EDTA. GnRH was then spiked in equal amounts into each sample. The results of the heparin plasma tube were compared to the results from the EDTA plasma tube. A mean effect ≤±15% of the mean quantitative result for EDTA plasma samples satisfies the acceptability criteria. It was found that the matrix effect was within acceptable limits for plasma containing sodium heparin anticoagulant when compared to plasma containing potassium EDTA anticoagulant. This indicates that the assay can be used with blood treated with heparin.

Next, the effect of lipemia and hemolysis on the assay was determined. The effect of lipemia and hemolysis on the quantitative result was determined by spiking pooled patient plasma with 5% by volume of lipid solution or lysed red blood cells. The samples were run in quadruplicate. The acceptability criteria is a mean bias ≤±15%. It was found that the mean bias from normal plasma was within acceptable limits (<±15%) for lipemic samples, but was not within acceptable limits (i.e., >15%) for hemolyzed samples (Table 1).

TABLE 1

Effect of Lipemia and Hemolysis on GnRH
Method Validation: Lipemic and Hemolysis Effect on Measurement
Component(s): GnRH
Sample Matrix: Human Plasma with Lipemia and Hemolysis

| | Concentration (pg/mL) | | |
|---|---|---|---|
| Sample | Plasma | Lipemic | Hemolyzed |
| GnRH | 87.22 | 95.31 | 101.5 |
| | 88.90 | 97.64 | 106.4 |
| | 88.24 | 95.67 | 104.2 |
| | 92.03 | 91.37 | 102.0 |
| Mean | 89.10 | 95.00 | 103.5 |
| Mean Matrix Effect (%) | NA | 6.62 | 16.19 |
| n | 4 | 4 | 4 |

Next, the interference for the internal standard was evaluated. Internal standard [(U-$^{23}$C$_9$, $^{15}$N)-Tyr$^5$], [(U-$^{23}$C$_6$, $^{15}$N)-Leu$^7$], [(U-$^{19}$C$_5$, $^{15}$N)-Pro$^9$]-Gonadorelin) working solution was spiked into Millipore water and tested in quadruplicate to evaluate the presence of unlabeled analyte. The acceptability criteria is a response that is ≤20% of the mean GnRH LLOQ response at the same retention time. The results were satisfactory in that the internal standard [(U-$^{23}$C$_9$, $^{15}$N)-Tyr$^5$], [(U-$^{23}$C$_6$, $^{15}$N)-Leu$^7$], [(U-$^{19}$C$_5$, $^{15}$N)-Pro$^9$]-Gonadorelin) interference response was <20% of the mean LLOQ response.

b. Accuracy and Precision

Precision and accuracy were validated using three analytical batches. Intra-assay imprecision (% CV) was calculated in 3 assay runs with 6 replicates at different concentrations in blank plasma calibrators and pooled human plasma spiked with known amounts of GnRH. Inter-assay imprecision (% CV) was calculated using data from each of 3 assay runs (n=18). The acceptability criteria is defined as an intra- and inter-assay imprecision ≤20% at the LLOQ and ≤15% throughout the remainder of the range.

Intra-assay inaccuracy was calculated in 3 assay runs with 6 replicates at 4 different concentrations in blank plasma spiked with known amounts of GnRH. Inter-assay inaccuracy was calculated using data from each of 3 assay runs (n=18). The acceptability criteria is defined as intra- and inter-assay inaccuracy (% Bias) of ≤±20% at the LLOQ and ≤±15% at other concentrations.

Thus, six replicates of spiked quality control (QC) samples at approximately 30, 100, 400 and 800 pg/mL (Pool 1, Pool 2, Pool 3, and Pool 4) were prepared in pooled plasma to determine imprecision for GnRH. Also six replicates of calibrator samples at approximately 5, 10, 500 and 1000 pg/mL were prepared in blank human plasma to determine inaccuracy and imprecision for GnRH. The intra and inter assay inaccuracy (% bias) and imprecision (% CV) for the calibrators and QC (precision only) samples were ≤20% at the LLOQ (determined to be 10 pg/mL) and ≤15% at all other concentrations.

The analytical range of the assay is validated between 10 pg/mL (LLOQ) and 1000 pg/mL (ULOQ). Table 2A shows the data for intra-assay precision. Table 2B shows the data for inter-assay precision for 10, 500 and 1000 pg/mL; the assay did not have acceptable precision at 5 pg/mL with a % CV of 5.82 and 22.75 for intra-assay and inter-assay precision respectively). It was found that the assay has acceptable intra-assay precision and inter-assay precision with a LLOQ of 10 pg/mL.

TABLE 2A

GnRH Intra Assay Precision
GnRH - Pooled Human Plasma and Blank Plasma

| Assay No. | Intra-Assay % CV | | | | | | |
|---|---|---|---|---|---|---|---|
| | Pool 1 | Pool 2 | Pool 3 | Pool 4 | 10 | 500 | 1000 |
| 1 | 3.51 | 1.71 | 1.47 | 1.90 | 6.78 | 2.25 | 2.35 |
| 2 | 3.54 | 3.29 | 2.83 | 2.94 | 17.14 | 4.44 | 2.29 |
| 3 | 6.38 | 3.09 | 3.17 | 1.78 | 5.59 | 3.21 | 1.78 |

TABLE 2B

GnRH Inter Assay Precision
GnRH - Pooled Human Plasma and Blank Plasma

| | Pool 1 | Pool 2 | Pool 3 | Pool 4 | 10 | 500 | 1000 |
|---|---|---|---|---|---|---|---|
| Average | 28.35 | 89.08 | 373.16 | 647.63 | 9.58 | 497.56 | 986.22 |
| % CV | 4.61 | 2.81 | 2.60 | 2.21 | 11.51 | 3.31 | 2.04 |
| N | 18 | 18 | 18 | 18 | 18 | 18 | 18 |

The inter-assay accuracy was determined by calculating the percent bias for the samples of blank human plasma spiked to 5 pg/mL, 10 pg/mL, 500 pg/mL, and 1000 pg/mL and then assayed 6 times in three different runs. The sample at 5 pg/mL had an inter-day bias of −20.39,% and an intra-day bias of −2.38, which was not considered to be acceptable for a clinical assay due to the residual presence of GnRH in the blank matrix.

TABLE 3

GnRH Accuracy

| System Precision | 10 pg/mL | 500 pg/mL | 1000 pg/mL |
|---|---|---|---|
| Expected Result | 10 | 500 | 1000 |
| Average Result | 9.58 | 497.56 | 986.22 |
| % Bias (Inter-day) | −4.24 | −0.49 | −1.38 |
| % Bias (Intra-day) | −8.35 | −1.00 | −1.68 |

Spike and recovery experiments were performed using a pooled plasma QC containing low levels of GnRH. A pooled patient QC was spiked with GnRH standard. Recovery was performed by comparing the measured results of samples spiked with 50, 250 and 750 pg/mL of standard material against expected values. Samples were analyzed in quadruplicate. The acceptability criteria is defined such that the calculated concentration at each level should be within the range of 85 to 115 percent of the expected concentration. Results are shown in Table 4 where it can be seen that mean recoveries between 85-115% were observed for 50 pg/mL, 250 pg/mL and 750 pg/mL spikes confirming accuracy of measurement.

TABLE 4

GnRH Spike and Recovery
Pooled Human Plasma

| | Concentration Added (pg/mL) | | | |
|---|---|---|---|---|
| | 0.000 | 50.000 | 250.000 | 750.000 |
| | Concentration Measured (pg/mL) | | | |
| GnRH Pooled | 28.21 | 74.00 | 299.0 | 844.5 |
| Plasma | 27.02 | 77.56 | 287.7 | 817.1 |
| | 28.33 | 78.04 | 299.3 | 795.0 |
| | 28.65 | 75.89 | 286.5 | 866.7 |
| Mean | 28.053 | 76.373 | 293.125 | 830.825 |
| Expected Conc. | NA | 78.053 | 278.053 | 778.053 |
| Recovery (%) | NA | 97.85 | 105.42 | 106.78 |
| n | 4 | 4 | 4 | 4 | c. Sample Stability

The stability of samples containing the peptide GnRH was assessed. Whole blood stability was evaluated to simulate adverse sample handling by the clinician. Autosampler stability was evaluated using blank plasma calibrators and pooled patient plasma samples spiked to various concentrations as shown in Table 5. GnRH whole blood stability did not pass validation criteria for 48 hours at room temperature with 100 µg/mL Aprotinin added. The test was repeated at shorter time periods to determine the maximum acceptable stability time. GnRH was shown to be stable in whole blood with aprotinin for up to 8 hours at room temperature (Table 6). GnRH stock solution is stable for up to 376 days frozen at −70° C. GnRH internal standard solution is stable for up to 51 days refrigerated at 4° C.

TABLE 5

Concentrations Used to Study GnRH Stability

| | Pooled Human Plasma Target Values (pg/mL) | | | |
|---|---|---|---|---|
| Analyte | Low Level | Mid Level 1 | Mid Level 2 | High Level |
| GnRH | <30 | 100 | 400 | 800 |
| | Blank Human Plasma Target Values (pg/mL) | | | |
| Analyte | Low Level | | Mid Level | High Level |
| GnRH | 10 | | 500 | 1000 |

TABLE 6

GnRH Whole Blood Stability
Method Validation: Whole Blood Stability
Component(s): GnRH
Sample Matrix: Whole Blood with Aprotinin

| Sample | Concentration (pg/mL) | | | |
|---|---|---|---|---|
| | Baseline | 4 Hours Room Temperature | 8 Hours Room Temperature | 24 Hours Room Temperature |
| GnRH | 369.4 | 363.6 | 321.5 | 267.6 |
| | 358.8 | 376.8 | 328.2 | 262.3 |
| | 363.7 | 370.1 | 314.2 | 282.7 |
| | 355.1 | 358.1 | 323.5 | 261.4 |
| Mean | 361.8 | 367.2 | 321.9 | 268.5 |
| Bias (%) | NA | 1.49 | −11.03 | −25.78 |
| n | 4 | 4 | 4 | 4 |

Also, experiments indicated that GnRH is stable for 24 hours at 10° C. when stored in the autosampler. The autosampler stability was evaluated using calibrators and quality control samples (LLOQ, mid-range and ULOQ using both pooled plasma and blank plasma calibrators). Duplicate curves were included with the batch. The first calibration curve was injected, then after 24 hours, the remaining quality control and calibration curve samples were injected. Both calibration curves were used to ascertain accuracy of pooled patient and blank plasma controls. The acceptability criteria is defined such that the standard curve back-fit data should be 80-120% at LLOQ, 85-115% at other concentrations of expected curve values. Mean accuracy of each quality control sample should be ≤±20% at the LLOQ and ≤±15% at all other levels. It was found that GnRH analysis was not affected by storage in the autosampler at 10° C. for 24 hours.

d. Cross Validation

In these experiments, a minimum of 25 samples representing the physiological range for GnRH were analyzed via LC-LC-MS/MS and RIA for assay-to-assay comparison. The acceptability criteria is defined as a scatter plot having a linear fit to the slope of 0.85 to 1.15. Mean bias, expressed as a percentage, should be ≤20% of the original RIA result. As shown in Table 7, cross-validation of samples analyzed by RIA (GnRH) against LC-LC-MS/MS indicates acceptable bias. Comparison using a scatter plot (FIG. 12) produces acceptable linearity between RIA and LC-LC-MS/MS for GnRH. A second experiment is shown as FIG. 8F.

TABLE 7

GnRH Cross-validation of Radioimmunoassay to LC-LC-MS/MS
Method Validation: Cross Validation of LC-LC-MS/MS
with RIA for GnRH
Component(s): GnRH
Sample Matrix: Human Plasma Samples

| Sample # | Concentration (pg/mL) | | |
|---|---|---|---|
| | RIA | LC-LC-MS/MS | Bias (%) |
| Sample 1 | 137.70 | 138.1 | 0.29 |
| Sample 2 | 538.39 | 617.4 | 14.68 |
| Sample 3 | 57.04 | 45.63 | −20.00 |
| Sample 4 | 380.13 | 414.8 | 9.12 |
| Sample 5 | 217.18 | 219.8 | 1.21 |
| Sample 6 | 631.70 | 711.0 | 12.55 |
| Sample 7 | 69.87 | 72.35 | 3.55 |
| Sample 8 | 56.31 | 48.57 | −13.75 |
| Sample 9 | 524.48 | 490.7 | −6.44 |
| Sample 10 | 21.47 | 24.17 | 12.58 |
| Sample 11 | 535.30 | 556.0 | 3.87 |
| Sample 12 | 40.76 | 44.02 | 8.00 |
| Sample 13 | 236.79 | 276.8 | 16.90 |
| Sample 14 | 838.22 | 790.6 | −5.68 |
| Sample 15 | 18.33 | 17.06 | −6.93 |
| Sample 16 | 684.67 | 590.9 | −13.70 |
| Sample 17 | 406.13 | 432.1 | 6.39 |
| Sample 18 | 812.67 | 800.4 | −1.51 |
| Sample 19 | 33.86 | 27.16 | −19.79 |
| Sample 20 | 172.16 | 186.8 | 8.50 |
| Sample 21 | 871.74 | 799.5 | −8.29 |
| Sample 22 | 506.44 | 547.3 | 8.07 |
| Sample 23 | 46.16 | 26.17 | −43.31 |
| Sample 24 | 595.77 | 651.6 | 9.37 |
| Sample 25 | 107.16 | 131.5 | 22.71 |
| Sample 26 | 759.59 | 708.9 | −6.67 |
| Sample 27 | 32.94 | 35.53 | 7.86 |
| Sample 28 | 253.10 | 280.6 | 10.87 |
| Sample 29 | 63.47 | 76.62 | 20.72 |
| Sample 30 | 717.19 | 725.3 | 1.13 |
| Mean Bias = | | | 1.08 |

Bias (%) = (LC-LC-MS/MS result − RIA result)/RIA result, expressed as a percentage
Samples were prepared by randomly spiking GnRH into different lots of pooled plasma.

Spiked standard samples at seven concentrations (10, 20, 50, 100, 250, 500 and 1,000 pg/mL) were used to generate a weighted (1/x) linear regression calibration curve, which covered the range from 10 to 1000 pg/mL for GnRH. The 5.0 pg/mL standard did not pass validation criteria as the LLOQ. Mean inaccuracies and imprecision <20% at the LLOQ and <15% at all other concentrations were observed. Correlation coefficients were >0.98.

e. Analytical Reportable Range

The lower limit of quantification (LLOQ) for GnRH using this assay was 10 pg/mL as determined during evaluation of inaccuracy, imprecision and calibration curve reproducibility. The upper limit of quantification using this assay was 1000 pg/mL for GnRH, as determined during evaluation of inaccuracy, imprecision and calibration curve reproducibility. Generally, aprotinin must be added to the sample at 100 μg/mL immediately following drawing of the sample for the assay to be most valid.

Example 2

Materials and Methods for Use of Assay to Measure GnRH a. Samples

The assay is expected to measure GnRH levels in human plasma samples. The lower limit of detection using a sample aliquot of 250 μL is 10 pg/mL for GnRH. Generally, aprotinin must be spiked into sample at 100 μg/mL immediately following the blood draw in order for results to be valid; separation of plasma from red blood cells should be in about ½ hour. The sample may then be stored and/or shipped frozen in plastic vial. For specimen collection, 1.0 mL can be used from and adult and/or a child; a minimum of 0.4 mL is recommended. For example, the samples generally are drawn into potassium EDTA or sodium heparin vacutainer tube. The tube is then inverted multiple times to mix the anticoagulant and aprotinin. The tube is then centrifuged and the plasma fraction removed and transferred to a labeled plastic vial and immediately frozen. For short term storage (i.e., about 2 weeks) the sample can be stored at −20° C. For long term storage (i.e., about 1 year) the sample should be stored at −70° C. Generally, hemolyzed samples are not acceptable.

b. Equipment

The following materials and/or equipment may be used. For preparation of the internal standards, GnRH (e.g., Polypeptide Labs) and isotopically labeled GnRH [(U-$^{23}$C$_9$, $^{15}$N)-Tyr$^5$], [(U-$^{23}$C$_6$, $^{15}$N)-Leu$^7$], [(U-$^{19}$C$_5$, $^{15}$N)-Pro$^9$]-Gonadorelin (Polypeptide Labs) may be used. For the blank matrix, human derived EDTA plasma, SeraCare Life Sciences, Inc. may be used. For mass spectrometry, an API 5000 Tandem Mass Spectrometer, Sciex, (Toronto, Canada) and a Turbo V™ Ion Source with ESI probe, Sciex, (Toronto, Canada) may be used. For HTLC, an Aria TX4 HTLC System, Cohesive Technologies, (MA, USA) consisting of 4 each: 1100 Series Quaternary Pump, 1100 Series Binary Pump, 1100 Series Vacuum Degasser may be used. As the autosampler, an HTS Twin PAL System Autosampler, CTC Analytics AG (Switzerland) may be used. For LC, Betasil Silica-100 Column, 2.1×50 mm, 5 μm particle size, Thermo Electron Corp., (USA) or Zorbax SB-C18 Column, 2.1×50 mm, 5 μm particle size, Agilent Inc., (USA) may be used for HILIC and RP respectively. An Analyst Version 1.4.1 or greater (Applied Biosystems, CA, USA) or Aria OS Version 1.5 or greater (Thermo) can be used to control the autosampler and switching valves for on-line liquid chromatography.

The following solvent preparations are also used: Eluting Pump A Mobile Phase (50 mM Ammonium Formate in Water); Loading Pump A Mobile Phase (10 mM Ammonium Formate in Water); Eluting/Loading Pump B Mobile Phase (100% Acetonitrile); Loading Pump C Mobile Phase (60:30:10 Acetonitrile:Isopropanol:Acetone); Needle Wash Solution 1 (Aqueous 1% Formic Acid) and Needle Wash Solution 2 (70:30 Acetonitrile:1N Ammonium Hydroxide).

c. Methods

A summary of the method used for LLE of the samples is as follows. Standards, samples and controls are thawed and mixed, with tubes provided for each standard, control, and patient. Duplicate standard curves are included with each analytical batch. An aliquot (e.g., 250 μL) of the standard, control or patient samples are pipetted into each tube and an aliquot (e.g., 50 μl) of the appropriate internal standard (IS) is added to each tube except double blanks. Tubes are mixed and acetonitrile (e.g., 1 mL) added to all tubes. Tubes are mixed, centrifuged at 3000 rpm for 5 minutes, and an aliquot (e.g., 900 μL) of solvent from each tube is transferred to a 96 deep well plate. The 96 well plate is then placed into turbovap 96 concentration workstation to evaporate the solvent. To evaporate the solvent, the timer is set for 75 minutes, the plate temperature is set to 60° C., and the nitrogen gas flow rate is set to 50 scfh (standard cubic feet per hour). Every 15 minutes, the nitrogen gas flow rate is increased by an increment of 15 scfh until the flow reaches 95 scfh. After 75 minutes, the plates are removed from the turbovap 96 concentration workstation and checked to make sure that all wells are completely dry. If not, the plate is returned to the turbovap for 15 more minutes. Each well is then reconstituted with 100 μL GnRH reconstitution solution (70:30 Millipore Type I Water: Methanol) and the plate is sealed (e.g., a heat-sealing foil) and after mixing, centrifuged at 3700 rpm at 10° C. for 10 minutes. The 96-well plate is then positioned in the in LC-MS/MS Autosampler.

LC-LC-MS/MS was performed as described below. For LC-LC purification of GnRH, the columns are: (1) a Zorbax SB-C-18, 2.1×50 mm, 5 um particle size (RP) extraction column and (2) a Betasil Silica-100, 2.1×50 mm, 5 um particle size analytical column. At step 4, the eluent is transferred from the extraction column at 0.5 mL/minute and chromato-focused with 1.5 mL/minute of acetonitrile provided by the eluting pump. GnRH and the stable labeled internal standard elute from the second column at approximately 3.5 minutes (+ or −1 minute).

For MS/MS a turbo spray MS/MS with a positive polarity is used with an MR pause of 5.007 msec using the parameters shown in Table 10A and 10B. As shown in Table 10A, there are two parent/daughter ion transitions for GnRH: 591.9/248.9 and 591.9/220.9. These are the two transitions shown in FIGS. 5-7. Also, shown are the two parent/daughter ion transitions for the labeled internal standard: 603.1/249.1 and 603.1/178.0. These transitions are also seen in FIGS. 5-7 as discussed above. A set up of the LC-LC-MS/MS system is shown in FIG. 13. A resulting MS/MS scan is shown in FIG. 14. For FIG. 14, GnRH SST peaks of 591.9/248.9 were analyzed for 100 pg/mL GNRH in 70:30 water:methanol.

TABLE 10A

MS/MS Peaks and Parameters for GnRH analysis

| @Q1 Mass (amu) | Q3 Mass (amu) | Dwell (msec) | Param | Start | Stop |
|---|---|---|---|---|---|
| 591.90 | 248.90 | 100.00 | CE | 37.00 | 37.00 |
| 591.90 | 220.90 | 75.00 | CE | 55.00 | 55.00 |
| 603.10 | 249.10 | 75.00 | CE | 37.00 | 37.00 |
| 603.10 | 178.00 | 100.00 | CE | 50.00 | 50.00 |

TABLE 10B

MS/MS Parameters for GnRH analysis Parameter Table:

| | |
|---|---|
| CAD: | 8.00 |
| CUR: | 30.00 |
| GS1: | 50.00 |
| GS2: | 80.00 |
| IS: | 4000.00 |
| TEM: | 550.00 |
| ihe: | ON |
| DP | 150.00 |
| EP | 8.00 |
| CXP | 15.00 |

The foregoing is considered as illustrative only of the principal of the invention. Since numerous modifications and changes will readily occur to those skilled in the art, it is not intended to limit the invention to the exact embodiments shown and described, and all suitable modifications and equivalents falling within the scope of the appended claims are deemed within the present inventive concept.

TABLE 8

GnRH 2D-LC Method
Loading Pump Buffer A: 10 mM Ammonium Formate in Water
Loading Pump Buffer B: Acetonitrile
Loading Pump Buffer C: 60:30:10 Acetonitrile:Isopropanol:Acetone
Eluting Pump Buffer A: 50 mM Ammonium Formate in Water
Eluting Pump Buffer B: Acetonitrile

| STEP | Start Time (min) | Step Duration (seconds) | Loading Pump (% A) | Loading Pump (% B) | Loading Pump (% C) | Flow Rate (mL/min) | Eluting Pump (% A) | Eluting Pump (% B) | Flow Rate (ml/min) | Eluting Pump Gradient Type |
|---|---|---|---|---|---|---|---|---|---|---|
| 1 | 0.00 | 20 | 90 | 10 | 0 | 1.0 | 5 | 95 | 3.0 | Isocratic |
| 2 | 0.33 | 40 | 70 | 30 | 0 | 1.0 | 5 | 95 | 3.0 | Isocratic |
| 3 | 1.00 | 30 | 55 | 45 | 0 | 1.0 | 0 | 100 | 1.0 | Isocratic |
| 4 | 1.50 | 20 | 46 | 54 | 0 | 0.5 | 0 | 100 | 1.5 | Isocratic |
| 5 | 1.83 | 20 | 10 | 90 | 0 | 1.0 | 5 | 95 | 1.0 | Isocratic |
| 6 | 2.17 | 70 | 0 | 100 | 0 | 1.5 | 27.5 | 72.5 | 1.0 | Gradient |
| 7 | 3.34 | 70 | 0 | 0 | 100 | 2.0 | 50 | 50 | 1.0 | Gradient |
| 8 | 4.50 | 30 | 90 | 10 | 0 | 1.2 | 50 | 50 | 2.0 | Isocratic |
| 9 | 5.00 | 70 | 90 | 10 | 0 | 1.0 | 90 | 10 | 1.5 | Isocratic |
| 10 | 6.17 | 20 | 90 | 10 | 0 | 1.0 | 5 | 95 | 1.0 | Isocratic |

That which is claimed is:

1. A method for quantifying an analyte in a sample comprising the steps of:
   (a) providing a sample containing an analyte;
   (b) chromatographically separating the analyte from other components in the sample using reverse phase liquid chromatography to obtain a chromatographically separated sample comprising the analyte;
   (c) transferring the chromatographically separated sample directly to a hydrophilic interaction analytical column, wherein the transferring is performed automatically on-line by a heart-cutting, chromato-focusing, or column switching technique;
   (d) concentrating the analyte in the chromatographically separated sample using hydrophilic interaction liquid chromatography to obtain a chromatographically concentrated sample comprising the analyte, wherein the analyte that is chromatographically separated in step (b) is the same compound that is concentrated in step (d); and
   (e) analyzing the chromatographically concentrated sample by mass spectrometry to quantify the analyte in the sample.

2. The method of claim 1, wherein the step of chromatographically separating the analyte from other components in the sample comprises the steps of: (i) applying at least a portion of the sample comprising the analyte to a reverse phase liquid chromatography extraction column; and (ii) eluting at least a portion of the analyte from the reverse phase liquid chromatography column; and the concentrating the analyte in the chromatographically separated sample comprises the steps of: (iii) applying at least a portion of the analyte eluted from the reverse phase liquid chromatography extraction column onto a hydrophilic interaction liquid chromatography analytical column; and (iv) eluting at least a portion of the analyte from the hydrophilic interaction liquid chromatography analytical column.

3. The method of claim 1, wherein the hydrophilic interaction liquid chromatography column provides an increase in sensitivity for detection of the analyte as compared to using only the reverse phase liquid chromatography column.

4. The method of claim 1, further comprising partially purifying the analyte from other components in the sample prior to the step of chromatographically separating the analyte from other components in the sample.

5. The method of claim 4, wherein the step of partially purifying the analyte from other components in the sample prior to chromatographic separation comprises at least one of: (i) liquid-liquid extraction; (ii) solid-phase extraction; (iii) dialysis to separate a population of analyte molecules that are not bound to proteins from a population of analyte molecules that are protein-bound; (iv) binding of the analyte to an antibody that recognizes the analyte as an antigen; or (v) diluting a portion of the analyte into a solvent such that proteins in the sample precipitate.

6. The method of claim 1, wherein the mass spectrometry comprises tandem mass spectrometry.

7. The method of claim 1, wherein the mass spectrometry is at least one of electrospray mass spectrometry or nanospray mass spectrometry.

8. The method of claim 1, wherein the analyte is at least one of a peptide, a polypeptide, or a protein.

9. The method of claim 8, wherein the peptide is Gonadotropin Releasing Hormone (GnRH).

10. The method of claim 9, wherein the step of analyzing the GnRH by mass spectrometry comprises ionizing the chromatographically separated GnRH to produce one or more GnRH ions having a mass/charge ratio comprising at least one of a parent ion of 591.9±0.5, or a daughter ion of 248.9 ±0.5 or 220.9 ±0.5, and detecting the ions by mass spectrometry, wherein the presence or amount of the GnRH ions is related to the presence or amount of GnRH in the sample.

11. The method of claim 10, wherein the presence or amount of GnRH ion is related to the presence or amount of GnRH in the sample by comparison to a stable isotope internal standard.

12. The method of claim 11, wherein the stable isotope internal standard is [(U-$^{23}$C$_9$, $^5$N)-Tyr$^5$], [(U-$^{23}$C$_6$, $^{15}$N)-Leu$^7$], [(U-$^{19}$C$_5$, $^{15}$N)-Pro$^9$]-GnRH.

13. The method of claim 12, wherein the stable isotope internal standard is detected by ionizing the stable isotope internal standard to produce one or more internal standard ions having a mass/charge ratio comprising at least one of a parent ion of 603.1±0.5, or a daughter ion of 249.1 ±0.5 or 178.0 ±0.5, and detecting the ions by mass spectrometry, wherein the presence or amount of the internal standard ions is related to the presence or amount of the internal standard.

14. The method of claim 9, wherein the measurement comprises a lower limit of quantitation for GnRH peptide of about 10 pg/mL.

15. The method of claim 9, wherein the measurement comprises an upper limit of quantitation for GnRH of about 1000 pg/mL.

16. The method of claim 1, wherein at least one of the separation step or the concentrating step is miniaturized.

17. A method for quantifying Gonadotropin Releasing Hormone (GnRH) in a sample comprising the steps of:
    (a) providing a sample containing GnRH;
    (b) chromatographically separating the GnRH from other components in the sample using reverse phase liquid chromatography to obtain a chromatographically separated sample comprising GnRH;
    (c) transferring the chromatographically separated sample directly to a hydrophilic interaction analytical column, wherein the transferring is performed automatically on-line by a heart-cutting, chromato-focusing, or column switching technique;
    (d) concentrating the GnRH in the chromatographically separated sample using hydrophilic interaction liquid chromatography to obtain a chromatographically concentrated sample comprising GnRH, wherein the GnRH that is chromatographically separated in step (b) is the same compound that is concentrated in step (d); and
    (e) analyzing the chromatographically concentrated sample by mass spectrometry to quantify the GnRH in the sample.

18. The method of claim 1, where the sample has a volume of 1 mL or less.

19. The method of claim 1, where the sample has a volume of 500 μL or less.

20. The method of claim 1, where the sample has a volume of 200 μL or less.

21. The method of claim 17, where the sample has a volume of 1 mL or less.

22. The method of claim 17, where the sample has a volume of 500 μL or less.

23. The method of claim 17, where the sample has a volume of 200 μL or less.

24. The method of claim 1, wherein the chromatographically separating step and the concentrating step occur on-line.

25. The method of claim 17, wherein the chromatographically separating step and the concentrating step occur on-line.

26. The method of claim 4, wherein the step of partially purifying the analyte from other components in the sample prior to chromatographic separation comprises removing phosphorylated, sulfated, or glucoronidated peptides from the sample.

27. The method of claim 17, further comprising partially purifying the analyte from other components in the sample prior to the step of chromatographically separating the analyte from other components in the sample.

28. The method of claim 27, wherein the step of partially purifying the analyte from other components in the sample prior to chromatographic separation comprises removing phosphorylated, sulfated, or glucoronidated peptides from the sample.

* * * * *

UNITED STATES PATENT AND TRADEMARK OFFICE
CERTIFICATE OF CORRECTION

PATENT NO.        : 9,091,695 B2
APPLICATION NO.   : 12/156391
DATED             : July 28, 2015
INVENTOR(S)       : Russell Philip Grant et al.

It is certified that error appears in the above-identified patent and that said Letters Patent is hereby corrected as shown below:

In the claims,

Column 37, Claim 12, Line 2, After "internal standard is", please delete "[(U-$^{23}$C$_9$, $^5$N)]", please insert -- [(U-$^{23}$C$_9$, $^{15}$N) --.

Signed and Sealed this
Fifth Day of January, 2016

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal pyroglutamate
<220> FEATURE:
<221> NAME/KEY: MOD_RES
<222> LOCATION: (10)..(10)
<223> OTHER INFORMATION: AMIDATION

<400> SEQUENCE: 1

Glu His Trp Ser Tyr Gly Leu Arg Pro Gly
1               5                   10

<210> SEQ ID NO 2
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal pyroglutamate
<220> FEATURE:
<221> NAME/KEY: MOD_RES
<222> LOCATION: (5)..(5)
<223> OTHER INFORMATION: Tyr5 is radiolabeled
<220> FEATURE:
<221> NAME/KEY: MOD_RES
<222> LOCATION: (7)..(7)
<223> OTHER INFORMATION: Leu7 is radiolabeled
<220> FEATURE:
<221> NAME/KEY: MOD_RES
<222> LOCATION: (9)..(9)
<223> OTHER INFORMATION: Pro9 is radiolabeled
<220> FEATURE:
<221> NAME/KEY: MOD_RES
<222> LOCATION: (10)..(10)
<223> OTHER INFORMATION: AMIDATION

<400> SEQUENCE: 2

Glu His Trp Ser Tyr Gly Leu Arg Pro Gly
1               5                   10
```